(12) United States Patent  (10) Patent No.: US 9,309,278 B2
Liu et al.  (45) Date of Patent: Apr. 12, 2016

(54) METHOD FOR MODIFICATION OF ORGANIC MOLECULES

(75) Inventors: Chuan-Fa Liu, Singapore (SG); Fupeng Li, Singapore (SG)

(73) Assignee: Nanyang Technological University, Singapore (SG)

( * ) Notice: Subject to any disclaimer, the term of this patent is extended or adjusted under 35 U.S.C. 154(b) by 37 days.

(21) Appl. No.: 14/116,623

(22) PCT Filed: May 14, 2012

(86) PCT No.: PCT/SG2012/000168
§ 371 (c)(1),
(2), (4) Date: Jul. 7, 2014

(87) PCT Pub. No.: WO2012/158122
PCT Pub. Date: Nov. 22, 2012

(65) Prior Publication Data
US 2014/0316105 A1  Oct. 23, 2014

(30) Foreign Application Priority Data
May 13, 2011  (SG) ................................ 201103480-8

(51) Int. Cl.
*C07K 1/113* (2006.01)
*C07C 323/12* (2006.01)
(Continued)

(52) U.S. Cl.
CPC ............... *C07K 1/113* (2013.01); *C07C 69/533* (2013.01); *C07C 233/05* (2013.01); *C07C 319/18* (2013.01); *C07D 277/04* (2013.01);
(Continued)

(58) Field of Classification Search
None
See application file for complete search history.

(56) References Cited

U.S. PATENT DOCUMENTS

| 4,318,858 A | 3/1982 | Hirai et al. |
| 2009/0143608 A1* | 6/2009 | Herzog et al. ................ 558/437 |
| 2010/0010153 A1* | 1/2010 | Feuerhake et al. ............ 524/556 |

OTHER PUBLICATIONS

Yeung et al. Tuning Specific Biomolecular Interactions Using Electro-switchable Oligopeptide Surfaces. Advanced Functional Materials. 2010, vol. 20, No. 16, pp. 2657-2657—Supporting Information.*

(Continued)

*Primary Examiner* — Jeffrey E Russel
(74) *Attorney, Agent, or Firm* — Wolf, Greenfield & Sacks, P.C.

(57) ABSTRACT

The present invention is directed to a method of alkylating a thiol group (R—S—H) or seleno group (R—Se—H) in a target molecule wherein the method comprises: reacting a target molecule comprising at least one thiol group with a compound of formula (I) or (II):

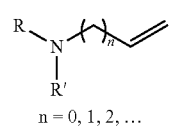

$n = 0, 1, 2, \ldots$

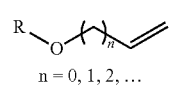

$n = 0, 1, 2, \ldots$

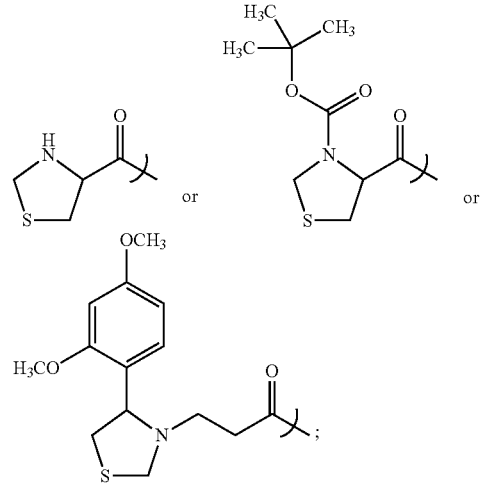

wherein R is an acetyl group or any other acyl group or is a group comprising any one of:

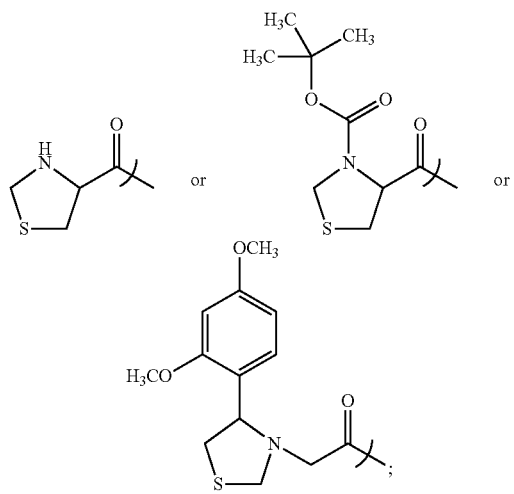

or wherein R in formula (II) can also be an alkyl group; and wherein R' is selected from a group consisting of a hydrogen, a methyl group and an ethyl group. In certain cases, the described methods may be used to install acetylated lysine analogs in target molecules (e.g., peptides, proteins).

18 Claims, 24 Drawing Sheets

(51) Int. Cl.
| | |
|---|---|
| C07C 323/25 | (2006.01) |
| C07C 319/18 | (2006.01) |
| C07K 1/107 | (2006.01) |
| C07C 69/533 | (2006.01) |
| C07C 233/05 | (2006.01) |
| C07K 14/00 | (2006.01) |
| C07D 277/04 | (2006.01) |
| C07D 277/06 | (2006.01) |

(52) U.S. Cl.
CPC ............ *C07D277/06* (2013.01); *C07K 1/1077* (2013.01); *C07K 14/00* (2013.01); *G01N 2440/10* (2013.01); *G01N 2440/12* (2013.01)

(56) References Cited

OTHER PUBLICATIONS

Valkevich et al. Forging Isopeptide Bonds Using Thiol-Ene Chemistry . . . Journal of the American Chemical Society. Apr. 12, 2012, vol. 134, pp. 6916-6919 + Supporting Information.*

International Search Report and Written Opinion dated Oct. 22, 2012 for Application No. PCT/SG2012/000168.

International Preliminary Report on Patentability (Chapter II) dated Aug. 19, 2013 for Application No. PCT/SG2012/000168.

European Search Report dated Sep. 11, 2014 for Application No. EP12786579.8.

Chinese Office Action dated Dec. 9, 2014 for Application No. CN201280023730.

Gómez-García et al., Probing secondary carbohydrate-protein interactions with highly dense cyclodextrin-centered heteroglycoclusters: the heterocluster effect. J Am Chem Soc. Jun. 8, 2005;127(22):7970-1.

Lanza et al., Radical additions of thiols to alkenes and alkynes in ionic liquids. Current Organic Chem. 2009;13(17):1726-32.

Li et al., A direct method for site-specific protein acetylation. Angew Chem Int Ed Engl. Oct. 4, 2011;50(41):9611-4. Epub Sep. 16, 2011.

Mattila et al., Derivatization of phosphopeptides with mercapto- and amino-functionalized conjugate groups by phosphate elimination and subsequent Michael addition. Org Biomol Chem. Aug. 21, 2005;3(16):3039-44. Epub Jul. 13, 2005.

Merbouh et al., 3-Mercaptopropanol as a traceless linker for chemical and enzymatic synthesis of oligosaccharides. Org Lett. Feb. 15, 2007;9(4):651-3.

Mustapa et al., Synthesis of orthogonally protected lanthionines. J Org Chem. Oct. 17, 2003;68(21):8185-92.

Triola et al., Racemization-free synthesis of S-alkylated cysteines via thiol-ene reaction. J Org Chem. May 2, 2008;73(9):3646-9. Epub Apr. 1, 2008.

Yeung et al., Tuning specific biomolecular interactions using electroswitchable surfaces. Advanced Functional Materials. 2010;20(16):2657-63.

* cited by examiner

SEQUENCE LISTING

<160> NUMBER OF SEQ ID NOS: 31

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 1

Phe Gln Pro Lys Cys Gly
1               5

```
<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (8)..(8)
<223> OTHER INFORMATION: AMIDATION

<400> SEQUENCE: 2

Val Gly Cys Ala Glu Lys Ser Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (7)..(7)
<223> OTHER INFORMATION: AMIDATION

<400> SEQUENCE: 3

Trp Ala Cys Tyr Lys Ser Leu
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: BIOTINYLATED
<220> FEATURE:
<221> NAME/KEY: MOD_RES
<222> LOCATION: (15)..(15)
<223> OTHER INFORMATION: AMIDATION

<400> SEQUENCE: 4

Gly Lys Gly Gly Ala Cys Arg His Arg Lys Val Leu Arg Asp Asn
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: BIOTINYLATED
<220> FEATURE:
<221> NAME/KEY: MOD_RES
<222> LOCATION: (14)..(14)
<223> OTHER INFORMATION: AMIDATION

<400> SEQUENCE: 5

Gly Cys Gly Gly Cys Gly Leu Gly Cys Gly Gly Ala Cys Arg
1               5                   10

<210> SEQ ID NO 6
<211> LENGTH: 6
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 6

Phe Gln Pro Lys Ser Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 7

Phe Gln Pro Lys Lys Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is N-acetyl-4-thialysine
<220> FEATURE:
<221> NAME/KEY: MOD_RES
<222> LOCATION: (6)..(6)
<223> OTHER INFORMATION: AMIDATION

<400> SEQUENCE: 8

Phe Gln Pro Lys Xaa Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: Xaa is N-acetyl-4-thialysine
<220> FEATURE:
```

```
<221> NAME/KEY: MOD_RES
<222> LOCATION: (8)..(8)
<223> OTHER INFORMATION: AMIDATION

<400> SEQUENCE: 9

Val Gly Xaa Ala Glu Lys Ser Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: Xaa is N-acetyl-4-thialysine
<220> FEATURE:
<221> NAME/KEY: MOD_RES
<222> LOCATION: (7)..(7)
<223> OTHER INFORMATION: AMIDATION

<400> SEQUENCE: 10

Trp Ala Xaa Tyr Lys Ser Leu
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: BIOTINYLATED
<220> FEATURE:
<221> NAME/KEY: MOD_RES
<222> LOCATION: (6)..(6)
<223> OTHER INFORMATION: Xaa is N-acetyl-4-thialysine
<220> FEATURE:
<221> NAME/KEY: MOD_RES
<222> LOCATION: (15)..(15)
<223> OTHER INFORMATION: AMIDATION

<400> SEQUENCE: 11

Gly Lys Gly Gly Ala Xaa Arg His Arg Lys Val Leu Arg Asp Asn
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: BIOTINYLATED
<220> FEATURE:
<221> NAME/KEY: MOD_RES
<222> LOCATION: (2)..(2)
<223> OTHER INFORMATION: Xaa is N-acetyl-4-thialysine
<220> FEATURE:
<221> NAME/KEY: MOD_RES
<222> LOCATION: (5)..(5)
<223> OTHER INFORMATION: Xaa is N-acetyl-4-thialysine
<220> FEATURE:
<221> NAME/KEY: MOD_RES
<222> LOCATION: (9)..(9)
<223> OTHER INFORMATION: Xaa is N-acetyl-4-thialysine
<220> FEATURE:
```

```
<221> NAME/KEY: MOD_RES
<222> LOCATION: (13)..(13)
<223> OTHER INFORMATION: Xaa is N-acetyl-4-thialysine
<220> FEATURE:
<221> NAME/KEY: MOD_RES
<222> LOCATION: (14)..(14)
<223> OTHER INFORMATION: AMIDATION

<400> SEQUENCE: 12

Gly Xaa Gly Gly Xaa Gly Leu Gly Xaa Gly Gly Ala Xaa Arg
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is thialysine
<220> FEATURE:
<221> NAME/KEY: MOD_RES
<222> LOCATION: (6)..(6)
<223> OTHER INFORMATION: AMIDATION

<400> SEQUENCE: 13

Phe Gln Pro Lys Xaa Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 14

Phe Gln Pro Lys Lys Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is N-methyl N-acetyl-4-thialysine
<220> FEATURE:
<221> NAME/KEY: MOD_RES
<222> LOCATION: (6)..(6)
<223> OTHER INFORMATION: AMIDATION
```

```
<400> SEQUENCE: 15

Phe Gln Pro Lys Xaa Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is a product of a thiol-ene coupling
      reaction between a cysteine residue and vinyl acetate
<220> FEATURE:
<221> NAME/KEY: MOD_RES
<222> LOCATION: (6)..(6)
<223> OTHER INFORMATION: AMIDATION

<400> SEQUENCE: 16

Phe Gln Pro Lys Xaa Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is a product of a thiol-ene coupling
      reaction between a cysteine residue and N-allylacetamide
<220> FEATURE:
<221> NAME/KEY: MOD_RES
<222> LOCATION: (6)..(6)
<223> OTHER INFORMATION: AMIDATION

<400> SEQUENCE: 17

Phe Gln Pro Lys Xaa Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (6)..(6)
<223> OTHER INFORMATION: C-terminal vinyl amide addition

<400> SEQUENCE: 18

Arg Leu Tyr Arg Ala Gly
1               5

<210> SEQ ID NO 19
<211> LENGTH: 37
<212> TYPE: DNA
<213> ORGANISM: Artificial Sequence
```

```
<220> FEATURE:
<223> OTHER INFORMATION: Synthetic Polynucleotide

<400> SEQUENCE: 19
gtctgatatt tgccggctgt cagctggagg atggccg                              37

<210> SEQ ID NO 20
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 20
cggccatcct ccagctgaca gccggcaaat atcagac                              37

<210> SEQ ID NO 21
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 21
ggtaaaggtg gtgcttgccg tcaccgtaaa gttc                                 34

<210> SEQ ID NO 22
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 22
gaactttacg gtgacggcaa gcaccacctt tacc                                 34

<210> SEQ ID NO 23
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 23
gaggacacca acctggccgc catccacgcc aag                                  33

<210> SEQ ID NO 24
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 24
cttggcgtgg atggcggcca ggttggtgtc ctc                                  33

<210> SEQ ID NO 25
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 25
aaggcagcca ggtgctccgc tcctgctacc                                      30
```

<210> SEQ ID NO 26
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 26
agcaggagcg gagcacctgg ctgccttggt g                          31

<210> SEQ ID NO 27
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (4)..(4)
<223> OTHER INFORMATION: ACETYLATION

<400> SEQUENCE: 27

Gln Pro Lys Lys
1

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 28

Arg Leu Tyr Arg Ala Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (5)..(5)
<223> OTHER INFORMATION: C-terminal thioester

<400> SEQUENCE: 29

Arg Leu Tyr Arg Ala
1               5

<210> SEQ ID NO 30
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 30
ggtggtcata tgcagatctt tgtgaag                               27

<210> SEQ ID NO 31
<211> LENGTH: 37
<212> TYPE: DNA
<213> ORGANISM: Artificial Sequence
<220> FEATURE:
<223> OTHER INFORMATION: Synthetic Polynucleotide

```
<400> SEQUENCE: 31
ctggtcaggt gggataccct ccttgtcttg aattttg                      37
```

METHOD FOR MODIFICATION OF ORGANIC MOLECULES

RELATED APPLICATIONS

This application is a national stage filing under 35 U.S.C. §371 of International Application No. PCT/SG2012/000168, filed May 14, 2012, which claims priority to Singapore Application No. 201103480-8, filed May 13, 2011, the contents of all of which are incorporated herein by reference in their entirety.

FIELD OF INVENTION

The present invention relates to a method for alkylation of organic molecules.

BACKGROUND

Post-translational modification (PTM) is a fundamental mechanism for modulating protein function. One such PTM with increasingly recognized significance is protein lysine (Lys) acetylation. Like Tyrosine (Tyr)/Serine (Ser)/Threonine (Thr) phosphorylation, Lys acetylation is a reversible biochemical process, where a lysine acetyltransferase adds an acetyl group onto the ε-amine of a lysine residue. A deacetylase acts in the opposite way to remove it. Initially discovered in histones, lysine acetylation has also been observed recently in a very large number of other proteins, suggesting its diverse regulatory functions in the cell. There is mounting evidence that aberrant lysine acetylation is implicated in many disease conditions such as cancer and neurological disorders. Therefore, the study of lysine acetylation biology is of great importance and will lead to continuous therapeutic innovations.

Although many years of intensive research have firmly established a broad role for lysine acetylation as a histone epigenetic mark affecting chromatin structure and function, the effects of most individual acetylation events—especially those identified more recently—remain to be elucidated. Recent research in genetics, cell biology and especially proteomics has identified lysine acetylation in a large number of non-histone proteins. The functions of most of these modifications are unknown. As a major limiting factor, the study of protein lysine acetylation is often hindered by a lack of homogeneous protein samples containing the acetylated lysine ("Lys-Ac") residue(s) of interest. Such homogenously acetylated proteins would be invaluable reagents for discerning the structural and functional effects of a particular Lys-Ac PTM via biophysical and biochemical means.

Several methods are useful to prepare site-specific modified proteins, such as unnatural amino-acid mutagenesis using the amber stop codon/suppressor tRNA pair, and protein chemical synthesis, but there remain significant technical barriers for the wide use of these methods by the bioscience research community at large. For example, unnatural amino acid mutagenesis is not widely available because it is a proprietary technology, and protein chemical synthesis requires extensive expertise of a well-trained chemist and is technically very challenging as well as labor-intensive.

Another known method is based on the combined use of unnatural amino acid mutagenesis and chemical modification to generate an acetyl-lysine analog but the optical purity is lost on the modified amino acid. Enzymatic Lys acetylation of recombinant proteins would appear to be an attractive approach. However, given the promiscuity of lysine acetyltransferases and the incomplete nature of enzymatic reactions, it is difficult if not impossible to isolate or characterize the desired acetylation product for structural and functional investigations.

As for other enzymatic reactions that do offer the necessary specificity, they often must work in the context of large macromolecular complexes such as with the help of other adaptor molecules, which renders them of little practical value.

A chemical approach for selective installation of acetylated Lys residues in recombinant proteins is therefore highly desired. Evidently, with the presence of many possible lysine residues in a normal protein, direct acetylation of a particular lysine residue is chemically not feasible.

The unique reactivity of the thiol group of cysteine (Cys) as a soft nucleophile has been exploited extensively for selective protein modification. Previously, a chemical method was developed to install a close isosteric analog of N-methyl-lysine into recombinant proteins (See Scheme I below). The method is based on a traditional alkylation reaction of the thiol group of a Cys residue with aminoethyl bromide or chloride, yielding aminoethylcysteine which is known to be a lysine equivalent.

When the alkylating agent is changed to N-methylaminoethyl halide, an N-methylated aminoethylcysteine residue or N-methyl thiaLys ("thiaLys(Me)") is generated, which has been shown to be functionally similar to the natural Lys(Me).

Scheme I

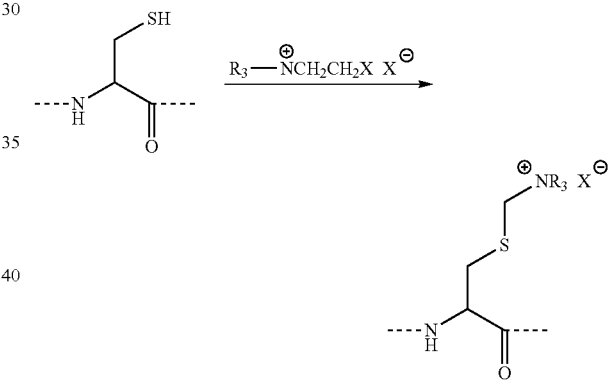

$R_3$ = $H_3$ or H, H, $CH_3$ or H, $CH_3$, $CH_3$ or $(CH_3)_3$
X = Cl or Br

As such, similar strategies have been proposed to prepare a close mimic of the native Lys(Ac) residue by making use of the unique reactivity of the cysteine thiol group. However, attempts to alkylate the Cys thiol with a similar N-acetyl-aminoethyl bromide and N-acetyl-aziridine failed to give the desired product (See Scheme IIa).

Further efforts in the prior art led to the development of methylthiocarbonyl-aziridine as the alkylating agent to afford methylthiocarbonyl-thiaLys as an N-acetyl-Lys mimic (See Scheme IIb). Although the alkylation reaction was successful and the resultant methylthiocarbonyl-thiaLys was shown to be recognized by a bromodomain-containing protein and by anti-acetyl-Lys antibodies, the presence of a large sulfur atom between the carbonyl and methyl in the thiocarbamate moiety makes it only a distant analog of the acetamide part in Lys (Ac). From both steric and electrochemical viewpoints, there are obvious and considerable differences between the acetyl and methylthiocarbonyl group (see structure in Scheme IIb), which may explain why the thiocarbamate modification is resistant to histone deacetylase cleavage.

Scheme II

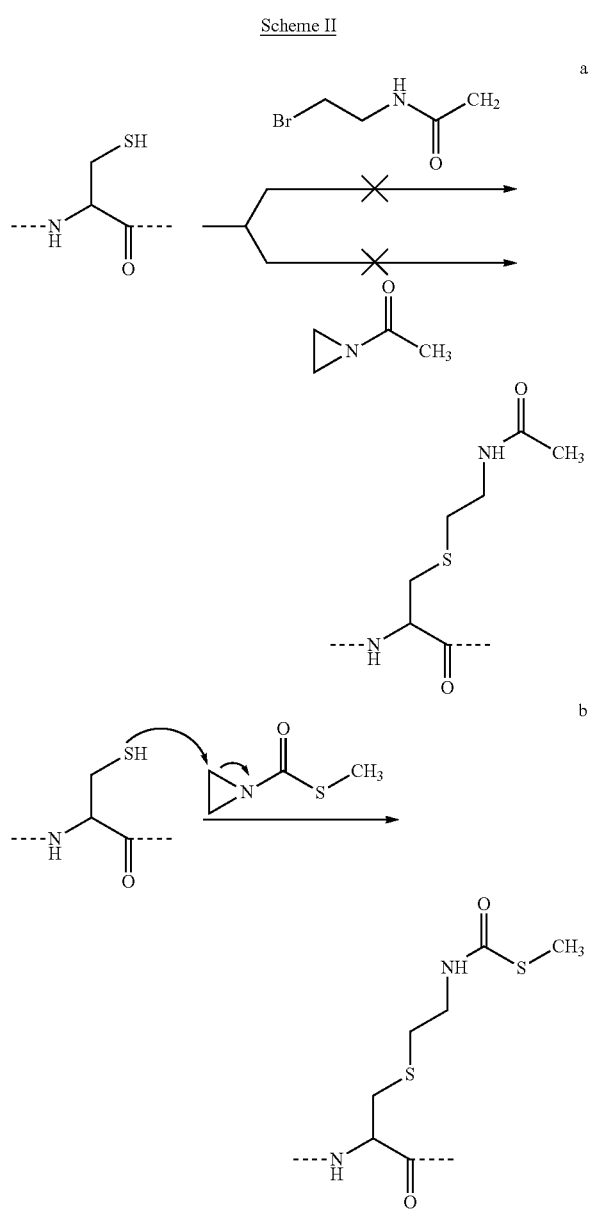

Clearly, analogous to 2-aminoethyl-cysteine (i.e., thialysine) and N-methyl-thialysine being ideal mimics of lysine and N-methyl-lysine respectively, the best mimic of Lys(Ac) would still be N-acetyl-4-thialysine or sLys(Ac) in which the thioether linkage is a close isosteric replacement of the γ-methylene group in natural Lys(Ac). As the position of this substitution is rather far away—by 2 carbon atoms—from the acetamide nitrogen, little differences are expected between this Lys(Ac) mimic and its natural counterpart in their exhibited physicochemical and biochemical properties. Unfortunately, current attempts to use a similar alkylation reaction with N-acetyl-aminoethyl bromide or iodide and N-acetyl-aziridine are unsuccessful at producing acetyl-thialysine with acceptable yields and selectivity.

Furthermore, nucleophilic substitution with an alkyl halide or the equivalent aziridine compound (Scheme IIa) cannot be used to selectively alkylate the thiol under conditions that are acceptable for a protein, so a different alkylation method must be provided.

Accordingly, there is a need to provide a method for alkylating the thiol group of Cys to obtain a Lys(Ac) mimic that overcomes or ameliorates one or more disadvantages disclosed above. Additionally, such a method will also be useful for installing other modifications (e.g., pegylation and ubiquitination) onto a thiol-containing compound such as a peptide or a protein.

SUMMARY

In a first aspect, there is provided a method of alkylating a thiol group (R—S—H) or seleno group (R—Se—H) in a target molecule wherein the method comprises: reacting a target molecule comprising at least one thiol group with a compound of formula (I) or (II):

$n = 0, 1, 2, \ldots$

$n = 0, 1, 2, \ldots$ wherein R is an acetyl group or any other acyl group or is a group comprising any one of:

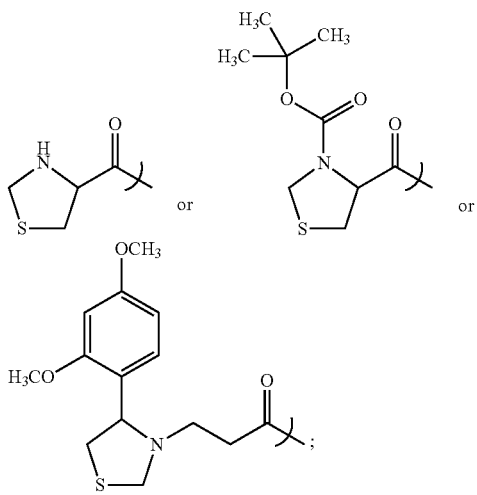

or wherein R in formula (II) can also be an alkyl group; and wherein R' is selected from a group consisting of a hydrogen, a methyl group and an ethyl group.

In one embodiment, the target molecule is an organic compound. In one embodiment, the organic compound is a peptide or a protein molecule. In still another embodiment, the peptide is selected from an oligopeptide, a polypeptide or a synthetic peptide. In yet another embodiment, the protein molecule is selected from the group consisting of a recombinant protein and a protein complex. One important aspect of the disclosed method resides in its ability to be performed on protein molecules under conditions which would not denature the protein or compromise its structural integrity.

In one embodiment, the disclosed method advantageously provides a simple, one-step process for modifying one or more amino acid residues present on a target molecule, such as biotin, histone or ubiquitin. In one embodiment, the disclosed method is capable of modifying specific amino acid residues to form ideal mimics of acetylated lysine. In one embodiment, the disclosed method selectively modifies one or more cysteine residues on the target molecule to form ideal mimics of acetylated lysine. More particularly, the disclosed method is directed to the alkylation of one or more cysteine residues via reaction with an appropriate alkylation agent to form acetylated lysine analogs. The type of acetylated lysine analog formed depends on the specific alkylating agent used in the reaction.

In one embodiment, the alkylation agent is a compound of formula (I) or (II) as described above. Advantageously, the inventors have found that the alkylation agent is capable of reacting with the thiol group present on the cysteine residue to form N-acetyl-4-thialysine, in which the thioether linkage is a close isosteric replacement of the 4-methylene group in natural acetylated lysine. As the position of this substitution is sterically distant from the acetamide nitrogen (by two carbon atoms), little differences are detected between the mimic and the natural acetylated lysine in physicochemical and biochemical properties.

Advantageously, the disclosed method overcomes technical problems of feasibility, low yield and low selectivity which plague the prior art methods. In contrast, the disclosed method is very robust and provides near 100% yield of the Lys-Ac mimics (e.g., N-acetyl-4-thialysine) in considerably shorter reaction times of from 30 minutes to 2 hours or less.

In another aspect, there is provided the use of a compound of Formula (I) as defined above as an alkylating agent for alkylation of a target molecule.

In yet another aspect, there is provided the use of a compound of Formula (II) as defined above as an alkylating agent for alkylation of a target molecule comprising a thiol-group (R—S—H) or a seleno group (R—Se—H).

In still another aspect, there is provided the use of a compound of Formula (I) for installing an acetylated lysine residue analog in a target molecule.

In another aspect, there is provided a pharmaceutical composition comprising a target molecule modified according to the method as defined above.

DEFINITIONS

The following words and terms used herein shall have the meaning indicated:

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Disclosure on Optional Embodiments

Exemplary, non-limiting embodiments of the method according to the first aspect will now be disclosed.

In one embodiment, the disclosed method comprises alkylating a thiol group of a target molecule, wherein the thiol group is the thiol group of a cysteine and/or a selenocysteine residue. In one embodiment, the thiol group is the thiol group of a cysteine residue.

In one embodiment, the R group of the compound of formula (I) or (II) may be an acyl group, wherein the acyl group is an aliphatic acyl group, or an alicyclic acyl group, or an aromatic acyl group, or an amino acyl or a peptidyl group or a proteinyl group.

In one embodiment, the R group of formula (I) or (II) is an aliphatic acyl group, which is selected from the group consisting of a linear aliphatic acyl group, a branched aliphatic acyl group, a tert-butyloxycarbonyl group, a derivative of a tert-butyloxycarbonyl group, a benzyloxycarbonyl group and a derivative of a benzyloxycarbonyl group.

In one embodiment, the acyl group is selected from the group consisting of a linear aliphatic acyl group having 1 to 20 or 1 to 7 carbon atoms; a branched aliphatic acyl group having 1 to 7 carbon atoms; and a polyethylene glycol) moiety.

In another embodiment, the acyl group is selected from the group consisting of formyl group, acetyl group, propionyl group, 2-propionyl group, butyryl group, isobutyryl group, pentanoyl group, hexanoyl group, allylcarbonyl group, cyclohexylmethylcarbonyl group, and $C_3$-$C_6$ cycloalkylcarbonyl groups, such as cyclopropylcarbonyl group, cyclopentylcarbonyl group, cyclohexylcarbonyl group, and 1 cyclohexenylcarbonyl group.

In yet another embodiment, the R group of formula (I) or (II) is an aromatic acyl group, which is selected from the group consisting of benzoyl group, 4-methylbenzoyl group, and 4-methoxybenzoyl group.

In another embodiment, the R group in Formula (II) is an alkyl group, wherein the alkyl group is selected from the group consisting of methyl, ethyl, n-propyl, i-propyl, n-butyl, t-butyl, sec-butyl, pentyl, hexyl, octyl, nonyl, decyl, undecyl, dodecyl, tridecyl, tetradecyl, pentadecyl, hexadecyl, octadecyl, poly(ethylene glycol)-ethyl and poly(ethylene glycol)-propyl. Exemplary alkyl groups may include, but are not limited to, $HO(CH_2CH_2O)_n$—$CH_2CH_2$—; $CH_3O(CH_2CH_2O)_n$—$CH_2CH_2$—; and $CH_3O(CH_2CH_2O)_n$—$CH_2CH_2CH_2$—.

In one embodiment, the alkylating agent is a compound of formula (I), where R is an acetyl group and R' is hydrogen and n is 0 (i.e., N-vinyl acetamide or "NVA").

In yet another embodiment, the alkylating agent is a compound of formula (I), wherein R is propionyl ($CH_3CH_2C(O)$—), R' is hydrogen and n is 0 (i.e., the alkylating agent is N-vinylpropionamide).

In still another embodiment, the alkylating agent is a compound of formula (I), wherein R is butyryl (CH₃CH₂CH₂C(O)—), R' is hydrogen and n is 0 (i.e., the alkylating agent is N-vinylbutyramide)

In another embodiment, the alkylating agent is a compound of formula (II), where R is CH₃C(O)—, i.e., vinyl acetate.

In another embodiment, the alkylating agent is a compound of formula (I), wherein R is CH₃C(O)—, R' is H and n is 1, i.e., N-allylacetamide.

In still another embodiment, the alkylating agent is a compound of formula (I), wherein R is CH₃C(O)—, R' is CH₃ and n is 0, i.e., N-methyl-N-vinylacetamide.

In yet another embodiment, the alkylating agent is a compound of formula (I), where the R is an acyl group selected from a peptidyl group or a proteinyl group, R' is H and n is 0.

In one embodiment, the alkylating reaction between NVA and a thiol group may be represented by Scheme III as shown below:

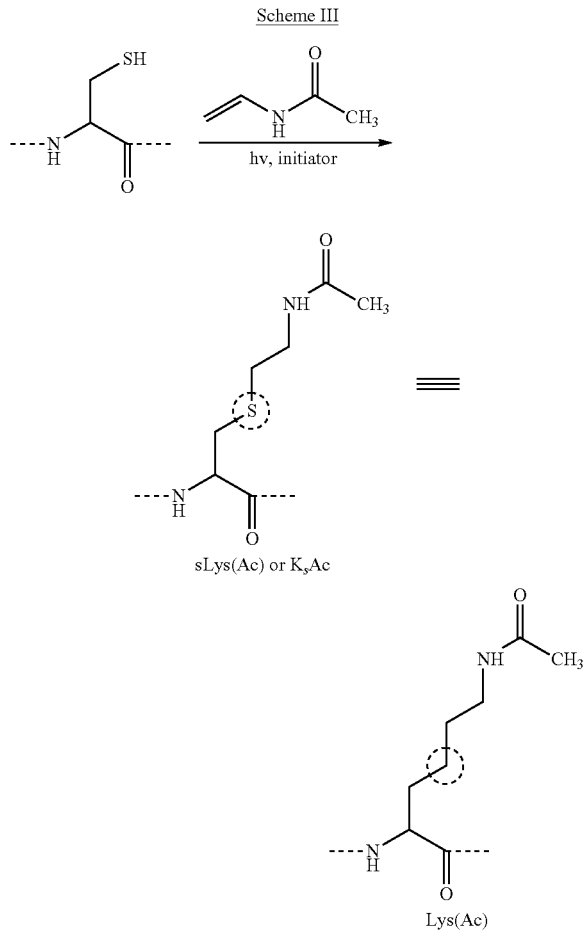

As can be seen from Scheme III, the thiol-ene coupling between the cysteine thiol and N-vinylacetamide directly generates the desired acetyl-thialysine in a single step reaction.

In one embodiment, the reaction mechanism for the reaction in Scheme III may be described in three general steps as shown in Scheme IV below:

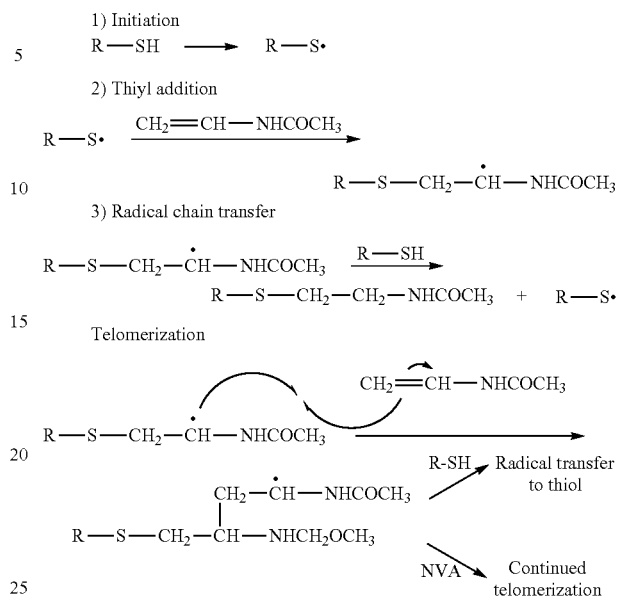

The disclosed method may further comprise a step of irradiating the reaction mixture with ultra-violet (UV) radiation. The irradiation step may further comprise the addition of photoinitiators into the reaction mixture. The photoinitiator may be a water soluble photoinitiator. The photoinitiator may be an azo-type initiator. In one embodiment, the photoinitiator is the compound 2,2'-Azobis[2-(2-imidazolin-2-yl)propane]dihydrochloride ("VA-044"). In another embodiment, the photoinitiator is the compound lithium phenyl-2,4,6-trimethylbenzoylphosphinate ("LAP").

The disclosed method may further comprise performing the alkylation reaction in the presence of an additional thiol compound. Advantageously, the additional thiol compound may serve to suppress the undesirable side reaction of radical chain telomerization. In one embodiment, the additional thiol compound may be selected for its ability to react with the radical intermediate formed by the addition of the thiyl radical to the NVA ethylene double bond to prevent the intermediate from reacting with another NVA molecule. In one embodiment, the additional thiol compound is glutathione. In one embodiment, the glutathione is used in its reduced form.

In one embodiment, the alkylation reaction may be performed in acetate buffer at pH 4 to 7 and in the presence of VA-044 as the initiator under UV irradiation at 365 nm.

In one embodiment, the molar ratio of the additional thiol compound to the NVA is about 3:10. In one embodiment, the molar ratio of the additional compound to the NVA to the photoinitiator is about 3:10:1.

In another embodiment, the molar ratio of the additional thiol compound to the NVA may be selected from the group consisting of 1:10, 2:10, 3:10, 4:10, 5:10, 6:10, 7:10, 8:10, 9:10 and 1:1.

The disclosed molar ratios may also apply to embodiments of the present invention where the alkylating agent is not NVA.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 5A shows a C18 analytical HPLC profile of the thiol-ene coupling reaction between peptide 1 and NVA at pH 6.0. Peak a: product; Peak b: disulfide-linked side product between peptide 1 and glutathione.

FIG. 5B shows an ESI-MS spectrum of peak a.

FIG. 5C shows an ESI-MS spectrum of peak b.

FIG. 11A shows a C18 analytical HPLC profile of the thiol-ene coupling reaction between ubiquitin K48C and NVA at pH 4.0. Peak a: ubiquitin K48C; Peak b: product.

FIG. 11B shows a MALDI-TOF MS spectrum of peak a.

FIG. 11C shows a MALDI-TOF MS spectrum of peak b.

FIG. 14A is a C4 semi-prep HPLC profile of the thiol-ene coupling reaction between H4 K16C and NVA at pH 7.0. Peak a: expected product; Peak b: oxidation product.

FIG. 14B is an ESI-MS spectrum of the raw and deconvoluted mass of peak a.

FIG. 15A is C4 semi-prep HPLC profile of the thiol-ene coupling reaction between H3 K27C and NVA at pH 4.0. Peak a: H3 K27C; Peak b: product.

FIG. 15B is an ESI-MS spectrum of the raw and deconvoluted mass of peak a.

FIG. 15C is an ESI-MS spectrum of the raw and deconvoluted mass of peak b.

FIG. 16A is a C18 analytical HPLC profile of peptide 1 with the installed acetyl-lysine analog in the SIRT2 assay. Peak a: deacetylated product; Peak b: Ac-FQPKK$_S$(Ac)G-NH$_2$ (SEQ ID NO: 8).

FIG. 16B is a C18 analytical HPLC profile of the native K(Ac)-peptide substrate in the SIRT2 assay. Peak c: deacetylated product; Peak d: native peptide substrate.

FIG. 16C is an ESI-MS spectrum of peak a. The sequence corresponds to SEQ ID NO: 13.

FIG. 16D is an ESI-MS spectrum of peak b. The sequence corresponds to SEQ ID NO: 8.

FIG. 16E is an ESI-MS spectrum of peak c. The sequence corresponds to SEQ ID NO: 14

FIG. 16F is an ESI-MS spectrum of peak d. The sequence corresponds to SEQ ID NO: 7.

FIG. 19A shows a C18 analytical HPLC profile of the thiol-ene coupling reaction between peptide 1 and N-vinyl-propionamide. Peak a: product; Peak b: peptide 1.

FIG. 19B shows an ESI-MS of peak a.

FIG. 20A shows a C18 analytical HPLC profile of the thiol-ene coupling reaction between peptide 1 and N-vinyl-butyramide. Peak a: product; Peak b: peptide 1; Peak *: unidentified peak.

FIG. 20B show an ESI-MS of peak a.

EXAMPLES

Non-limiting examples of the invention will be further described in greater detail by reference to specific Examples, which should not be construed as in any way limiting the scope of the invention.

In the following methods, the amino acids and coupling agents used were purchased from GL Biochem (Shanghai, China) and Novabiochem (Germany). The human sirtuin 2 (SIRT2) enzyme, NAD$^+$ and assay buffer were purchased from Enzo Life Sciences (New York, United States of America). The Histone H4 K16Ac antibody was from Active Motif (California, United States of America). All other chemical reagents were purchased from commercial suppliers.

Analytical and semi-prep HPLC were performed on a Shimadzu HPLC system equipped with a SPD-M20A prominence diode array detector. A C18 reverse-phase column (Jupiter 5 μm 300 A, 250*4.6 mm) was used for analytical HPLC. The C18 reversed-phase column (Jupiter 5 μm 300 A, 250*10 mm) and C4 reversed-phase column (Vydac 5 μm 300 A, 250*10 mm) were used for semi-prep HPLC. The analytes were eluted using a gradient mixture of two solvents: solvent A was deionized water containing 0.05% trifluoroacetic acid (TFA) and solvent B was 90% acetonitrile (ACN) in deionized water containing 0.05% TFA. The mobile phase flow rate was 1 mL/min for analytical HPLC and 2.5 mL/min for semi-prep HPLC.

Peptide or protein masses were measured using a Thermo FINNIGAN LCQ Deca XP MAX equipped with electrospray ionization (ESI) ion source or a 4800 MALDI TOF/TOF Analyzer using α-cyano-4-hydroxycinnamic acid as the matrix.

Example 1

Model Study of the Thiol-ene Coupling Reaction Between NVA and Benzyl Mercaptan

To demonstrate the thiol-ene coupling mechanism, different concentrations of N-vinyl-acetamide (NVA) and benzyl mercaptan (BM) were mixed in 0.2 M acetate buffer (at pH 4.0, prepared from acetic acid and sodium acetate). Thereafter, 5 mM of initiator VA-044 (2,2'-Azobis[2-(2-imidazolin-2-yl)propane]dihydrochloride) was added in a 0.5 ml thin wall, clear tube (Axygen, Inc., San Francisco, United States of America). The tube containing the reaction mixture was placed in a Cole Parmer 9818-series darkroom UV light box at about 10 cm under the lamp (365 nm) at room temperature for 30 min to obtain the reaction product, a small organic thiol compound benzyl mercaptan (BzSH).

Figure 1:
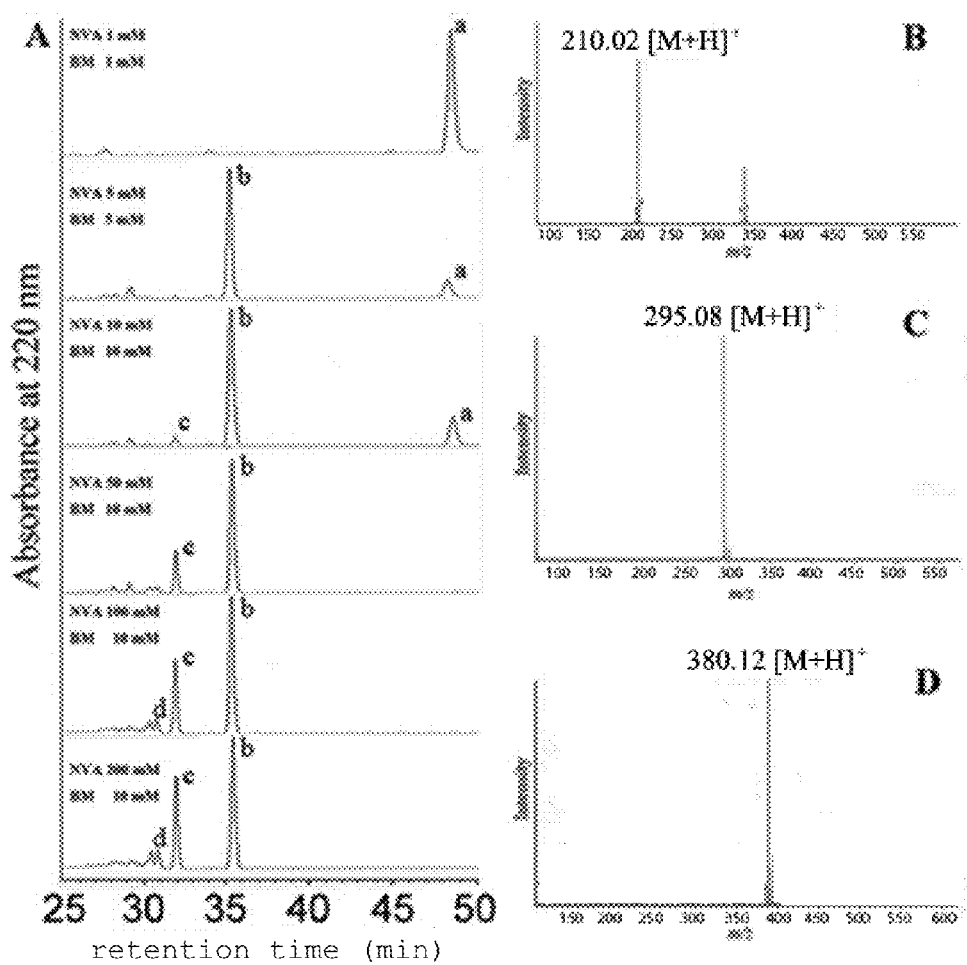
FIG. 1A is a C18 analytical high pressure liquid chromatogram ("HPLC") monitoring of the thiol-ene coupling reaction between benzyl mercaptan (BM) and N-vinyl-acetamide ("NVA") at pH 4.0, wherein peak a corresponds to BM; Peak b corresponds to product; Peak c corresponds to side product 1, i.e. NVA dimer attached to BM; and Peak d corresponds to side product 2, NVA trimer attached to BM.
FIG. 1B shows an electrospray ionization mass spectrometer ("ESI-MS") spectrum of peak b of FIG. 1A.
FIG. 1C shows an ESI-MS spectrum of peak c of FIG. 1A.
FIG. 1D shows an ESI-MS spectrum of peak d of FIG. 1A.

The reaction was monitored by C18 analytical HPLC and the results are shown in FIG. 1A. The results were also confirmed by electrospray ionization mass spectrometry (ESI-MS) and shown in FIGS. 1B, 1C and 1D. The HPLC conditions were 0% to 50% of buffer B in buffer A in 50 min.

As seen in FIG. 1A(i), when NVA and BM were at a concentration of 1 mM respectively, only a BM peak (denoted as peak a) was detected. No BzSH peak (denoted as peak b) was detected. In FIGS. 1A(ii) and 1A(iii), when NVA and BM were at a concentration of 5 mM and 10 mM respectively, the conversion to BzSH did not improve with prolonged irradiation time, as evidenced by the presence of peak a. As seen in FIGS. 1A(iv), 1A(v) and 1A(vi) where NVA was added in an excess amount as compared to BM, complete conversion to BzSH was obtained, as evidenced by the absence of the BM peak a.

However, in FIGS. 1A(iv), 1A(v) and 1A(vi), additional peaks c and d were observed. The presence of peak c was due to a side product of an NVA dimer attached to BM, and the presence of peak d was due to a side product of an NVA trimer attached to BM.

Peak b was further characterized by ESI-MS. In FIG. 1B, the mass spectrum of intensity versus the mass-to-charge ratio (m/z) of BzSH is shown. The [M+H]$^+$ found had a m/z value of 210.02 and a molecular weight of 209.09.

Peak c was further characterized by ESI-MS. In FIG. 1C, the mass spectrum of intensity versus the mass-to-charge ratio (m/z) of the NVA dimer side product is shown. The [M+H]$^+$ found had a m/z value of 295.08 and a molecular weight of 294.14.

Peak d was further characterized by ESI-MS. In FIG. 1D, the mass spectrum of intensity versus the mass-to-charge ratio (m/z) of the NVA trimer side product is shown. The [M+H]$^+$ found had a m/z value of 380.12 and a molecular weight of 379.19.

Figure 2:
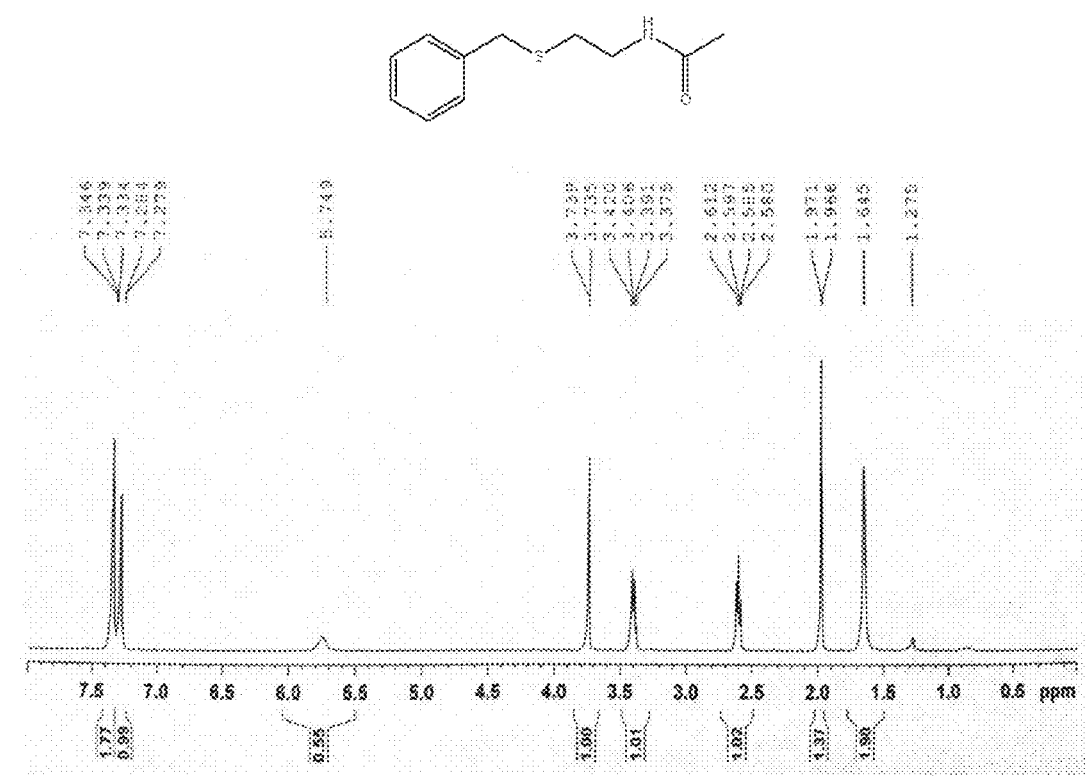
FIG. 2 shows a $^1$H NMR spectra of the reaction product of the thiol-ene reaction of FIG. 1.
Figure 3:
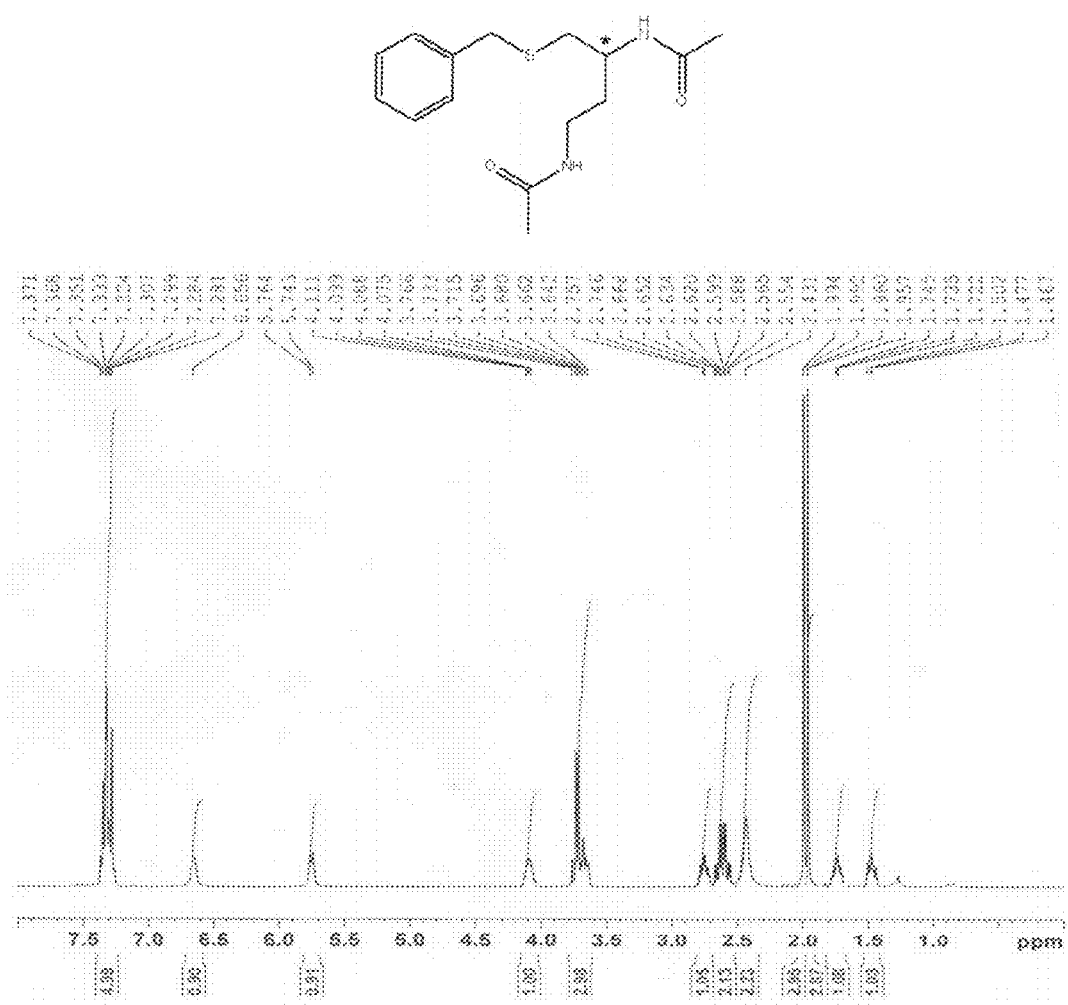
FIG. 3 shows a $^1$H NMR spectra of the side product of the thiol-ene reaction of FIG. 1.
Figure 4:
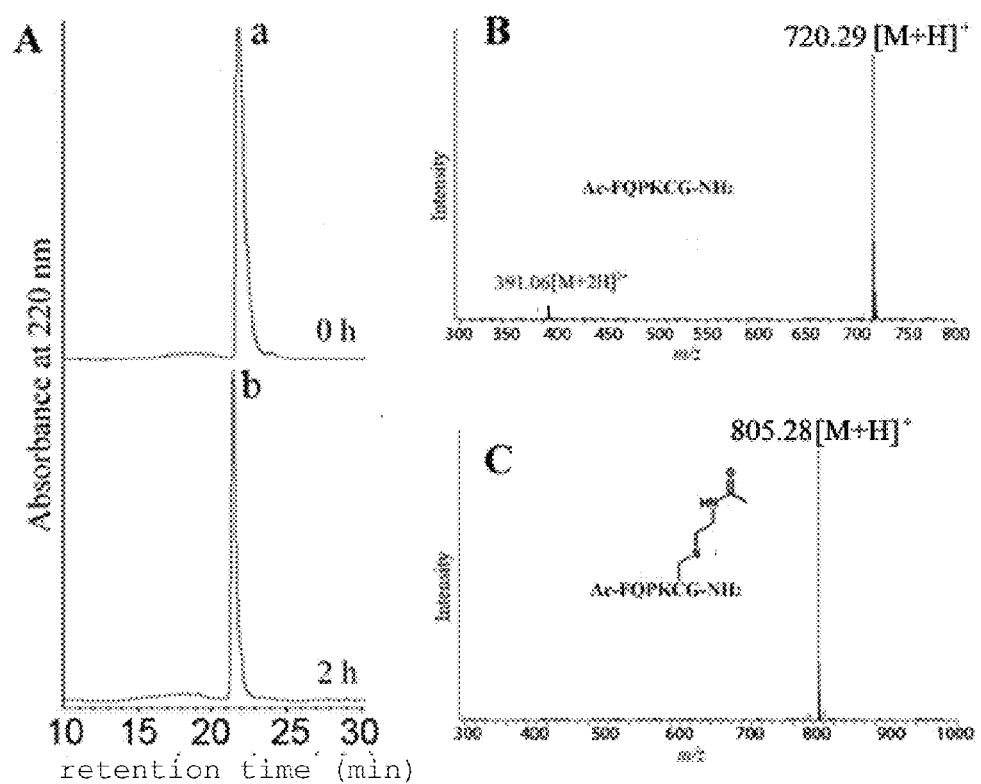
FIG. 4A shows a C18 analytical HPLC profile of the thiol-ene coupling reaction between peptide 1 and NVA at pH 4.0. Peak a: peptide 1; Peak b: product.
FIG. 4B shows an ESI-MS spectrum of peak a. The sequence corresponds to SEQ ID NO: 1.
FIG. 4C shows an ESI-MS spectrum of peak b. The sequence corresponds to SEQ ID NO: 8.
Figure 5:
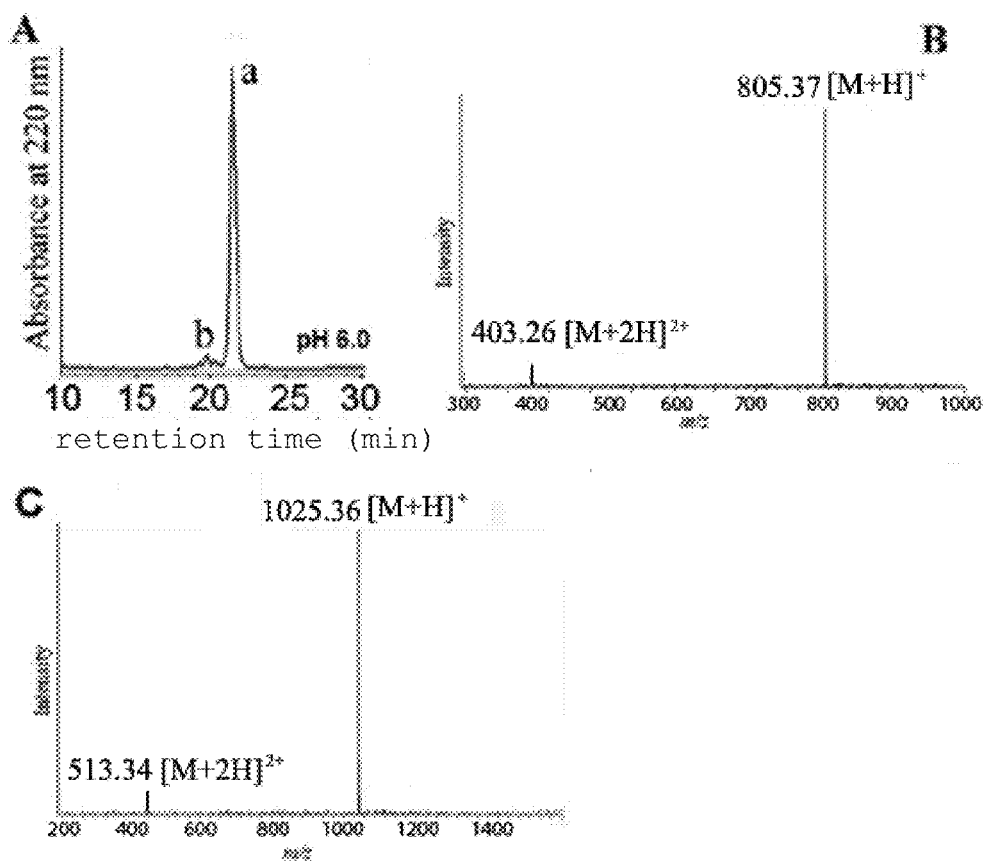
Figure 6:
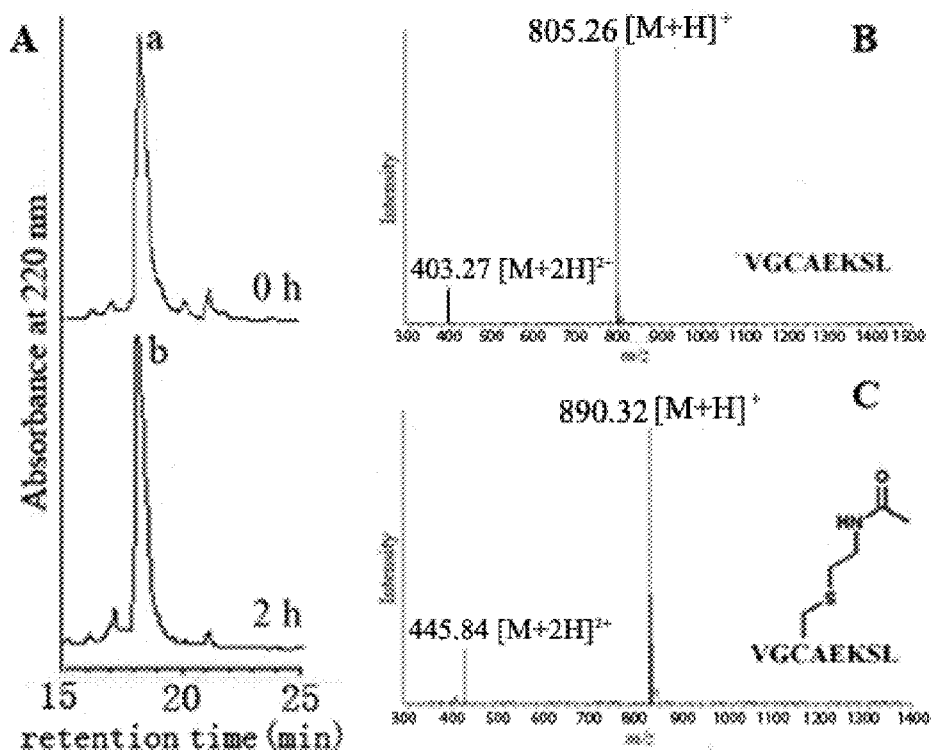
FIG. 6A shows a C18 analytical HPLC profile of the thiol-ene coupling reaction between peptide 2 and NVA at pH 4.0. Peak a: peptide 2; Peak b: product.
FIG. 6B shows an ESI-MS spectrum of peak a. The sequence corresponds to SEQ ID NO: 2.
FIG. 6C shows an ESI-MS spectrum of peak b. The sequence corresponds to SEQ ID NO: 9.
Figure 7:
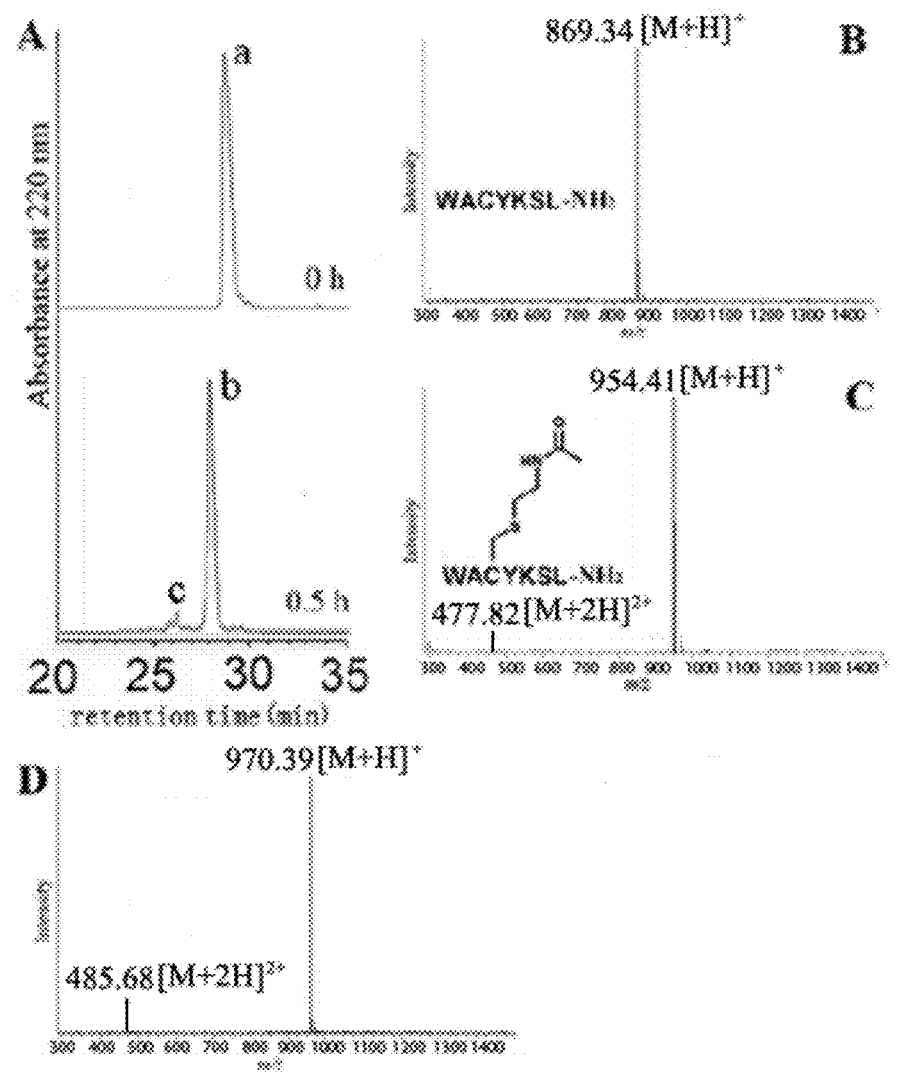
FIG. 7A shows a C18 analytical HPLC profile of the thiol-ene coupling reaction between peptide 3 and NVA at pH 4.0. Peak a: peptide 3; Peak b: expected product; Peak c: oxidation product.
FIG. 7B shows an ESI-MS spectrum of peak a. The sequence corresponds to SEQ ID NO: 3.
FIG. 7C shows an ESI-MS spectrum of the peak b. The sequence corresponds to SEQ ID NO: 10.
FIG. 7D shows an ESI-MS spectrum of the peak c.
Figure 8:
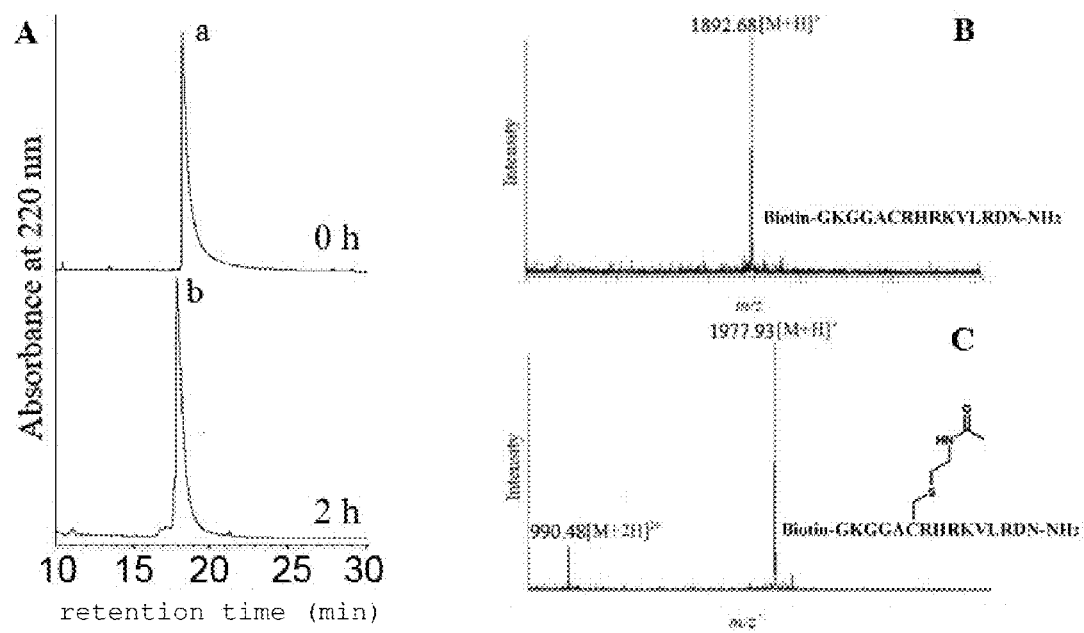
FIG. 8A shows a C18 analytical HPLC profile of the thiol-ene coupling reaction between peptide 4 and NVA at pH 4.0. Peak a: peptide 4; Peak b: product.
FIG. 8B shows a matrix assisted laser desorption/ionization-time of flight mass spectrometer ("MALDI-TOF MS") spectrum of peak a. The sequence corresponds to SEQ ID NO: 4.
FIG. 8C shows a MALDI-TOF MS spectrum of peak b. The sequence corresponds to SEQ ID NO: 11.

The molecular structure and the $^1$H NMR spectra of the reaction product, BzSH, (in deuterated chloroform (CDCL$_3$) solvent) is shown in FIG. 2. The molecular structure and the $^1$H NMR spectra of the NVA dimer side product (in CDCL$_3$ solvent) is shown in FIG. 3.

This example demonstrated the mechanism of the classic radical thiol-ene addition reaction and helps to explain the formation of the side products. The carbon radical formed at step 2, Scheme IV, is usually much more likely to react with a thiol molecule in the critical rate-limiting step of radical chain transfer (step 3, Scheme IV), which generates another thiyl radical. However, in the presence of a large excess of the -ene compound (NVA), the carbon radical can also sometimes react with another NVA molecule in a phenomenon called telomerization (See Scheme IV above). Therefore, addition of glutathione is capable of suppressing this side reaction as it can act as a radical chain transferring agent and participate in step 3, Scheme IV.

Examples 2-6 and Comparative Examples

Synthesis of Peptide Substrates for Alkylation

To obtain Cys-containing peptides, five model peptides were synthesized as C-terminal carboxyamides using standard fluorenylmethyloxycarbonyl (Fmoc) solid phase peptide synthesis techniques. Rink-amide 4-methylbenzhydrylamine (MBHA) resin was utilized for the synthesis. The Fmoc protection group was removed by treatment with 20% piperidine in dimethylformamide (DMF) twice (2 min for the first time and 20 min for the second time).

All the amino acids were mixed with 4 molar equivalents (eq.) of the resin, and the coupling was performed using 4 eq. of benzotriazol-1-yl-oxytripyrrolidinophosphonium hexafluorophosphate (PyBOP) and 8 eq. of N,N-diisopropylethylamine (DIEA) for 2 h.

In Examples 4 and 5, D-biotin was used at the last coupling step to synthesize peptide substrates 3 and 4, as detailed in Table 1 below. After sequence assembly, the final deprotection and cleavage was performed by using a cocktail of TFA: $H_2O$:triisopropylsilane: 2-mercaptoethanol in the ratio of 94:2.5:2.5:1 for 3 h at room temperature. The peptide was then precipitated with diethyl ether and lyophilized. The crude peptides were purified by C18 semi-prep HPLC.

The sequences of the Cys-containing peptides obtained in Examples 2 to 6 are listed in Table 1 below.

Furthermore, two control peptide substrates were synthesized without Cys residues: Ac-Phe-Gln-Pro-Lys-Ser-Gly-$NH_2$ (SEQ ID NO: 6) and Ac-Phe-Gln-Pro-Lys-Lys(Ac)-Gly-$NH_2$ (SEQ ID NO: 7).

Alkylation of Peptide Substrates 15 mM glutathione, 50 mM N-vinyl-acetamide (NVA) and 5 mM of initiator 2,2'-Azobis[2-(2-imidazolin-2-yl)propane] dihydrochloride (VA-044) in 0.2 M acetate buffer at pH 4 were mixed in a reaction tube to obtain a reaction mixture. The reaction mixture was added to each of the synthesized peptide substrates in the amounts detailed in Table 2 below.

The reaction tube was irradiated under 365 nm ultraviolet (UV) for 30 min or 1 h to obtain reaction products. The reaction products were analyzed by C18 analytical HPLC and confirmed by ESI or matrix-assisted laser desorption/ionization time-of-flight mass spectrometry (MALDI-TOF MS). The mass spectra are shown in FIGS. 4 to 8. MS analysis was done on either desalted samples (using a C18 zip-tip) or on HPLC-purified fractions.

TABLE 2

| Ex. | Substrate No. | Substrate | Amount (mM) | Reaction Time (h) | Yield (%) |
|---|---|---|---|---|---|
| 2 | 1 | Ac-*Phe-Gln-Pro-Lys-Cys-Gly*-$NH_2$<br>(Ac-FQPKCG-$NH_2$) (SEQ ID NO: 1) | 5 | 1 | >95 |
| 3 | 2 | H-*Val-Gly-Cys-Ala-Glu-Lys-Ser-Leu*-$NH_2$<br>(H-VGCAEKSL-$NH_2$) (SEQ ID NO: 2) | 5 | 1 | >95 |
| 4 | 3 | H-*Trp-Ala-Cys-Tyr-Lys-Ser-Leu*-$NH_2$<br>(H-WACYKSL-$NH_2$) (SEQ ID NO: 3) | 5 | 0.5 | 95 |
| 5 | 4 | Biotin-*Gly-Lys-Gly-Gly-Ala-Cys-Arg-His-Arg-Lys-Val-Leu-Arg-Asp-Asn*-$NH_2$<br>(Biotin-GKGGACRHRKVLRDN-$NH_2$)<br>(SEQ ID NO: 4) | 5 | 1 | >95 |
| 6 | 5 | Biotin-*Gly-Cys-Gly-Gly-Cys-Gly-Leu-Gly-Cys-Gly-Gly-Ala-Cys-Arg*-$NH_2$<br>(Biotin-GCGGCGLGCGGACR-$NH_2$)<br>(SEQ ID NO: 5) | 1.25 | 1 | 95 |

TABLE 1

| Ex. | No. | Substrate |
|---|---|---|
| 2 | 1 | Ac-*Phe-Gln-Pro-Lys-Cys-Gly*-$NH_2$<br>(Ac-FQPKCG-$NH_2$) (SEQ ID NO: 1) |
| 3 | 2 | H-*Val-Gly-Cys-Ala-Glu-Lys-Ser-Leu*-$NH_2$<br>(H-VGCAEKSL-$NH_2$) (SEQ ID NO: 2) |
| 4 | 3 | H-*Trp-Ala-Cys-Tyr-Lys-Ser-Leu*-$NH_2$<br>(H-WACYKSL-$NH_2$) (SEQ ID NO: 3) |
| 5 | 4 | Biotin-*Gly-Lys-Gly-Gly-Ala-Cys-Arg-His-Arg-Lys-Val-Leu-Arg-Asp-Asn*-$NH_2$<br>(Biotin-GKGGACRHRKVLRDN-$NH_2$) (SEQ ID NO: 4) |
| 6 | 5 | Biotin-*Gly-Cys-Gly-Gly-Cys-Gly-Leu-Gly-Cys-Gly-Gly-Ala-Cys-Arg*-$NH_2$<br>(Biotin-GCGGCGLGCGGACR-$NH_2$) (SEQ ID NO: 5) |

The C18 analytical HPLC profile of the reaction of Example 2 is shown in FIG. 4A. In FIG. 4A, peptide substrate 1 in Example 2 is denoted by peak a, while the reaction product is denoted by peak b.

Peak a was further characterized by ESI-MS. In FIG. 4B, the mass spectrum of intensity versus the mass-to-charge ratio (m/z) of the peptide substrate is shown. The $[M+H]^+$ found had a m/z value of 720.29 and a molecular weight of 719.34.

Peak b was further characterized by ESI-MS. In FIG. 4B, the mass spectrum of intensity versus the mass-to-charge ratio (m/z) of the reaction product is shown. The $[M+H]^+$ found had a m/z value of 805.28 and a molecular weight of 804.39.

The HPLC conditions used in Example 2 were 0% to 40% of buffer B in buffer A in 40 min.

A comparative example was done for peptide substrate 1 at pH 6 instead, with all other conditions kept the same. The C18 analytical HPLC profile of the reaction of the comparative example is shown in FIG. 5A. In FIG. 5A, the reaction product is denoted by peak a, while the disulfide-linked side product between peptide substrate 1 and glutathione is denoted by peak b.

Peak a was further characterized by ESI-MS. In FIG. 5B, the mass spectrum of intensity versus the mass-to-charge ratio (m/z) of the reaction product is shown. The [M+H]$^+$ found had a m/z value of 805.37 and a molecular weight of 804.39.

Peak b was further characterized by ESI-MS. In FIG. 5C, the mass spectrum of intensity versus the mass-to-charge ratio (m/z) of the side product is shown. The [M+H]$^+$ found had a m/z value of 1025.36 and a molecular weight of 1024.66.

In this comparative example, formation of a minute amount (i.e., less than 3%) of disulfide cross-linked side product between the peptide substrate and glutathione was detected. This seems due to the presence in the glutathione sample of a small amount of an oxidized form of glutathione, which at the higher pH of pH 6 underwent a disulfide exchange with the Cys thiol in the peptide substrate. At lower pH (e.g., pH 4), such an exchange reaction is inhibited. Accordingly, it can be concluded that a new and pure glutathione (reduced) sample should be used. Further, degassing of the buffer should be performed to prevent oxidation of the glutathione.

The HPLC conditions used in the comparative example were 0% to 40% of buffer B in buffer A in 40 min.

The C18 analytical HPLC profile of the reaction of Example 3 is shown in FIG. 6A. In FIG. 6A, peptide substrate 2 in Example 3 is denoted by peak a, while the reaction product is denoted by peak b.

Peak a was further characterized by ESI-MS. In FIG. 6B, the mass spectrum of intensity versus the mass-to-charge ratio (m/z) of the peptide substrate is shown. The [M+H]$^+$ found had a m/z value of 805.26 and a molecular weight of 804.42.

Peak b was further characterized by ESI-MS. In FIG. 6C, the mass spectrum of intensity versus the mass-to-charge ratio (m/z) of the reaction product is shown. The [M+H]$^+$ found had a m/z value of 890.32 and a molecular weight of 889.47.

The HPLC conditions used in Example 3 were 0% to 30% of buffer B in buffer A over 30 min.

The C18 analytical HPLC profile of the reaction of Example 4 is shown in FIG. 7A. In FIG. 7A, peptide substrate 3 in Example 4 is denoted by peak a, the expected reaction product is denoted by peak b and the oxidation product is denoted by peak c.

Peak a was further characterized by ESI-MS. In FIG. 7B, the mass spectrum of intensity versus the mass-to-charge ratio (m/z) of the peptide substrate is shown. The [M+H]$^+$ found had a m/z value of 869.34 and a molecular weight of 869.04.

Peak b was further characterized by ESI-MS. In FIG. 7C, the mass spectrum of intensity versus the mass-to-charge ratio (m/z) of the expected reaction product is shown. The [M+H]$^+$ found had a m/z value of 954.41 and a molecular weight of 954.09.

Peak c was further characterized by ESI-MS. In FIG. 7D, the mass spectrum of intensity versus the mass-to-charge ratio (m/z) of the oxidation reaction product is shown. The [M+H]$^+$ found had a m/z value of 970.39 and a molecular weight of 970.08.

The HPLC conditions used in Example 4 were 0% to 30% of buffer B in buffer A over 30 min.

The C18 analytical HPLC profile of the reaction of Example 5 is shown in FIG. 8A. In FIG. 8A, peptide substrate 4 in Example 5 is denoted by peak a and the reaction product is denoted by peak b.

Peak a was further characterized by MALDI-TOF MS. In FIG. 8B, the mass spectrum of intensity versus the mass-to-charge ratio (m/z) of the peptide substrate is shown. The [M+H]$^+$ found had a m/z value of 1892.68 and a molecular weight of 1890.99.

Peak b was further characterized by MALDI-TOF MS. In FIG. 8C, the mass spectrum of intensity versus the mass-to-charge ratio (m/z) of the reaction product is shown. The [M+H]$^+$ found had a m/z value of 1977.93 and a molecular weight of 1976.04.

The HPLC conditions used in Example 5 were 0% to 30% of buffer B in buffer A over 30 min.

Figure 9:
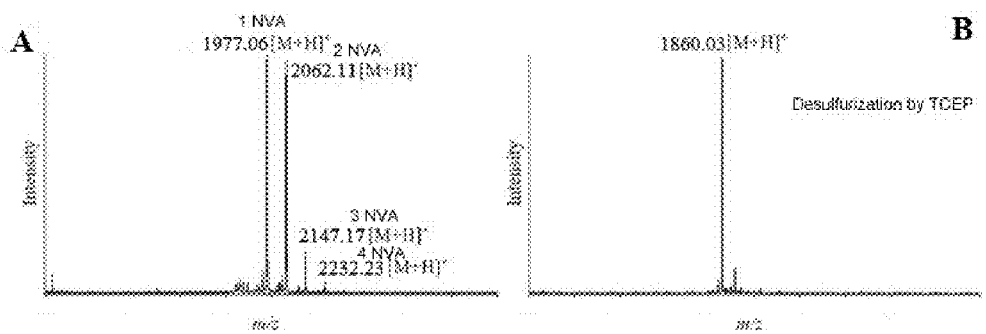
FIG. 9A shows a MALDI-TOF MS spectrum of the thiol-ene coupling reaction between peptide substrate 4 and NVA under non-standard conditions, i.e., when no glutathione was added (other conditions were the same).
FIG. 9B shows a MALDI-TOF MS spectrum of the product if 15 mM tris(2-carboxyethyl)phosphine ("TCEP") was added to replace glutathione.

Comparative examples were done for peptide substrate 4 under non-standard conditions. The MALDI-TOF MS of the reaction products when no glutathione was added, while keeping all other conditions the same, is shown in FIG. 9A. As seen in FIG. 9A, additional side products were detected in addition to the desired thiol-ene coupling product. The side products were because the Cys residue was alkylated by di-, tri- and tetrameric NVAs. Further, the MALDI-TOF MS of the reaction products when glutathione was replaced with 15 mM tris(2-carboxyethyl)phosphine (TCEP), keeping all other conditions the same, is shown in FIG. 9B. As seen in FIG. 9B, a desulfurization reaction took place to give a product with a −32 MW. Thus, addition of the reducing agent TCEP was actually detrimental to the reaction as it led to desulfurization of the peptide substrate.

Accordingly, it can be concluded that glutathione, together with peptide substrate 4, participated in the critical rate-limiting chain transfer step to effectively intercept (or quench) the carbon free radical intermediate which was formed at the addition step of the thiyl radical to the NVA ethylene double bond, thereby preventing it from reacting with another molecule of NVA. As expected, all the glutathione was also alkylated by NVA in the reaction.

Figure 10:
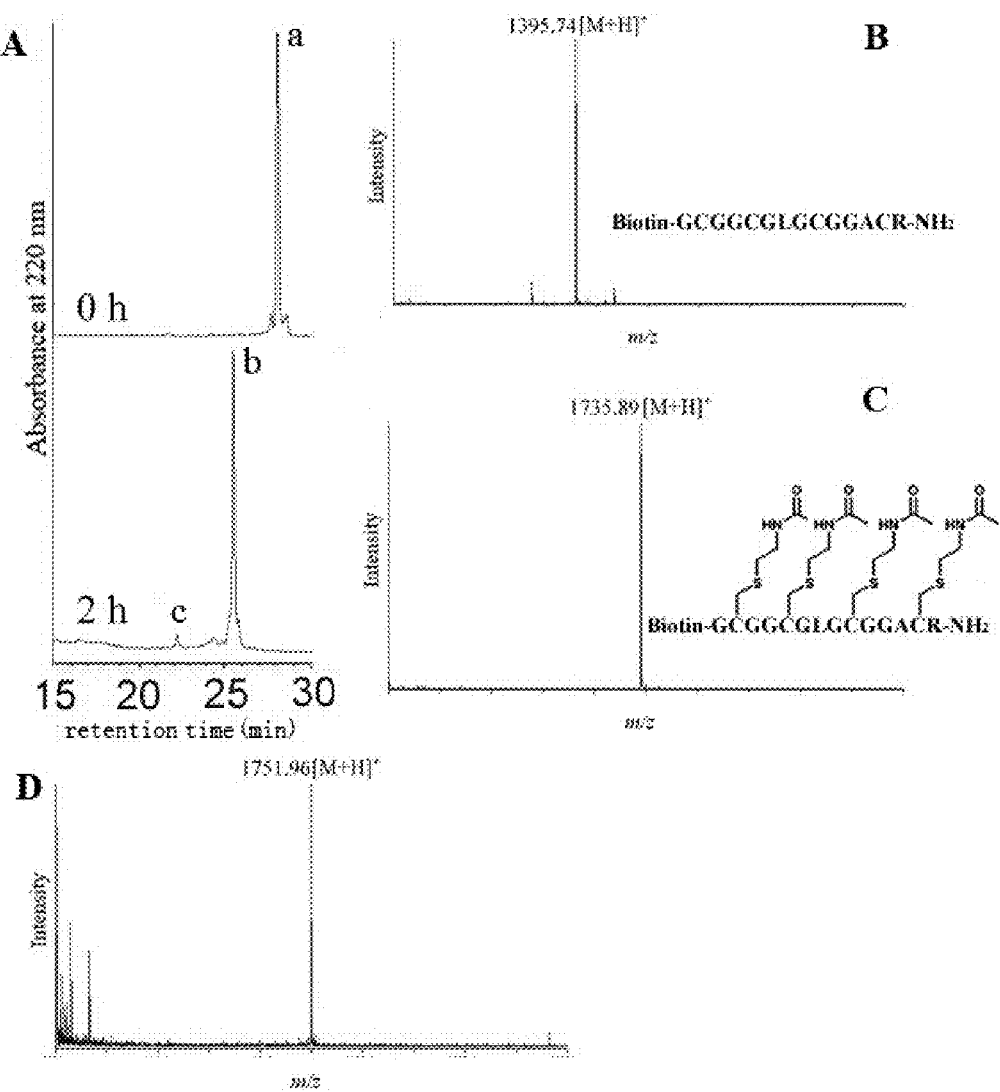
FIG. 10A shows a C18 analytical HPLC profile of the thiol-ene coupling reaction between peptide substrate 5 and NVA at pH 4.0; Peak a: peptide 5; Peak b: expected product; Peak c: oxidation product.
FIG. 10B shows a MALDI-TOF MS spectrum of peak a. The sequence corresponds to SEQ ID NO: 5.
FIG. 10C shows a MALDI-TOF MS spectrum of peak b. The sequence corresponds to SEQ ID NO: 12.
FIG. 10D shows a MALDI-TOF MS spectrum of peak c.

The C18 analytical HPLC profile of the reaction of Example 6 is shown in FIG. 10A. In FIG. 10A, peptide substrate 5 in Example 6 is denoted by peak a, the expected reaction product is denoted by peak b and the oxidized thiol product is denoted by peak c.

Peak a was further characterized by MALDI-TOF MS. In FIG. 10B, the mass spectrum of intensity versus the mass-to-charge ratio (m/z) of the peptide substrate is shown. The [M+H]$^+$ found had a m/z value of 1395.74 and a molecular weight of 1394.52.

Peak b was further characterized by MALDI-TOF MS. In FIG. 10C, the mass spectrum of intensity versus the mass-to-charge ratio (m/z) of the expected reaction product is shown. The [M+H]$^+$ found had a m/z value of 1735.89 and a molecular weight of 1734.72.

Peak c was further characterized by MALDI-TOF MS. In FIG. 10D, the mass spectrum of intensity versus the mass-to-charge ratio (m/z) of the oxidized thiol product is shown. The [M+H]$^+$ found had a m/z value of 1751.96 and a molecular weight of 1750.71.

The HPLC conditions used in Example 6 were 0% to 30% of buffer B in buffer A over 30 min.

It can thus be concluded from Example 6 that because peptide substrate 5 contains 4 Cys residues in its sequence, 1.25 mM of peptide 5 was sufficient to obtain the desired reaction product in a clean tetra-alkylating reaction with 95% yield, as shown in Table 2 above.

A comparative example was done with control peptide Ac-Phe-Gln-Pro-Lys-Ser-Gly-NH$_2$ (SEQ ID NO: 6), which has no Cys residue. No reaction product was detected.

Further comparative examples were done without UV irradiation. No reaction products were detected.

Examples 7 to 9

Synthesis of Protein Substrates for Alkylation

Preparation of Ubiquitin K48C

K48C point mutation was introduced to ubiquitin gene by QuikChange™ site-directed mutagenesis kit (Stratagene) with the primers:

```
                                       (SEQ ID NO: 19)
Ubi K48C F:
5'-GTCTGATATTTGCCGGCTGTCAGCTGGAGGATGGCCG-3';
and (SEQ ID NO: 20)
Ubi K48C R:
5'-CGGCCATCCTCCAGCTGACAGCCGGCAAATATCAGAC-3'.
```

The plasmid containing ubiquitin K48C gene was transformed into BL21 (DE3) cell. The cells were grown in 1 L LB media containing ampicillin to OD600 of 0.6 and induced by a final concentration of 0.5 mM IPTG for 4 h at 37° C. After centrifugation at 6000 rpm for 10 min at 4° C., cells were re-suspended in 50 ml lysis buffer (50 mM Tris-HCl, 100 mM NaCl, 1 mM DTT, pH 7.5) and broken by microfluidization (Microfluidics, Newton, USA). After centrifugation at 25,000 g for 30 min at 4° C., 70% perchloric acid was added to the supernatant at a ratio of 350 µl to 50 ml lysis buffer. The mixture was stirred for 10 min and centrifuged at 25,000 g for 30 min at 4° C. The supernatant was filtered with 0.2 µm filter and dialyzed with 3.5 KDa cut-off dialysis tubing against 50 mM ammonium acetate buffer (pH 4.5 with 1 mM DTT).

After filtration, the proteins were purified with a HiTrap™ SP FF 5 ml FPLC column (GE Healthcare Life Sciences). It was eluted with a linear gradient from 0% to 100% FPLC buffer B (50 mM ammonium acetate, pH 4.5, 1 mM DTT, 0.5 M NaCl) in buffer A (50 mM ammonium acetate, pH 4.5, 1 mM DTT) in 120 min at a flowrate 0.5 ml/min. Usually the ubiquitin would be eluted at around 240 mM NaCl. After FPLC purification, the proteins were dialyzed to ddH2O followed by lyophilization.

Preparation of H4 K16C

K16C point mutation was introduced to H4 gene by the same mutagenesis kit with the primers:

```
                                       (SEQ ID NO: 21)
H4 K16C F:
5'-GGTAAAGGTGGTGCTTGCCGTCACCGTAAAGTTC-3'
and (SEQ ID NO: 22)
H4 K16C R:
5'-GAACTTTACGGTGACGGCAAGCACCACCTTTACC-3'.
```

The plasmid containing H4 K16C gene was transformed into BL21 (DE3) pLysS cell. The cells were grown in 1 L LB media containing ampicillin and chloramphenicol to OD600 of 0.6 and induced by 0.4 mM IPTG for 3 h at 37° C. After centrifugation at 6000 rpm for 10 min, cells were re-suspended in 50 ml wash buffer (50 mM Tris-HCl, 100 mM NaCl, 1 mM DTT, pH 7.5) and broken by microfluidization. The cell debris was removed by centrifugation at 20,000 g for 30 min at 4° C. The pellet was washed with wash buffer containing 1% Triton X-100 twice and one time without Triton X-100. Then 1 ml of DMSO was added to the pellet and the pellet was stirred for 30 min. After that 10 ml unfolding buffer (6 M Guanidinium HCl, 10 mM Tris-HCl, 10 mM DTT, pH 7.5) was added. After centrifugation, the supernatant was loaded to a 26/60 Sephacryl S-200 column and purified with gel filtration buffer (7 M de-ionized Urea, 20 mM sodium acetate, 1 M sodium chloride, 5 mM beta-mercaptoethanol, 0.5 M EDTA, pH 5.2). After FPLC purification, the protein was purified again by C4 semi-prep HPLC followed by lyophilization.

Preparation of H3 K27C

The C110A point mutation was introduced to H3 gene by mutagenesis kit with the primers:

```
                                       (SEQ ID NO: 23)
H3 C110A F:
5'-GAGGACACCAACCTGGCCGCCATCCACGCCAAG-3';
and (SEQ ID NO: 24)
H3 C110A R:
5'-CTTGGCGTGGATGGCGGCCAGGTTGGTGTCCTC-3'.
```

The K27C point mutation was introduced to H3 C110A gene by mutagenesis kit with the primers:

```
                                       (SEQ ID NO: 25)
H3 K27C F:
5'-AAGGCAGCCAGGTGCTCCGCTCCTGCTACC-3';
and (SEQ ID NO: 26)
H3 K27C R:
5'-AGCAGGAGCGGAGCACCTGGCTGCCTTGGTG-3'.
```

The expression of H3 K27C protein was the same as that of H4 K16C.

Alkylation of Protein Substrates

Introduction of sLys(Ac) into Ubiquitin: Preparation of Ub K$_S$48Ac

The freeze-dried ubiquitin K48C was dissolved in the 0.2 M acetate buffer (pH 4.0 or pH 7.0). The final concentrations of the reactants were as follows:

Ubiquitin K48C: 0.5 mM.
NVA: 50 mM.
VA-044: 5 mM.
Glutathione: 15 mM.

Figure 11:
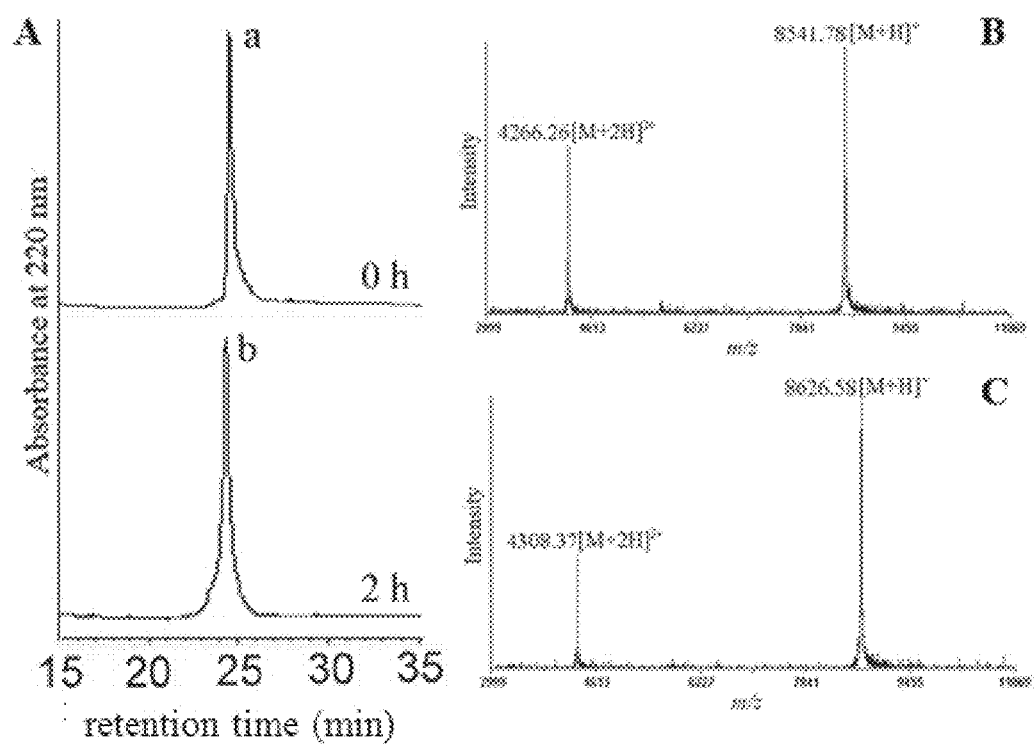
Figure 12:
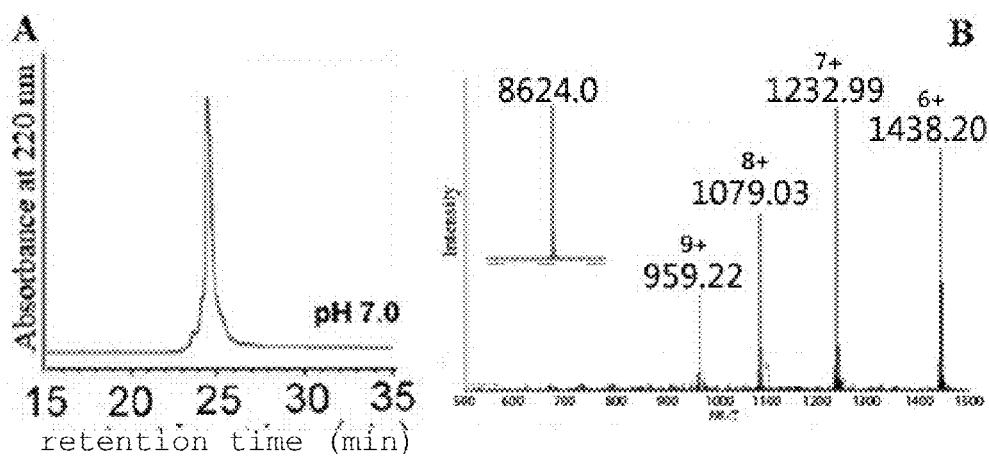
FIG. 12A shows a C18 analytical HPLC profile of the thiol-ene coupling reaction between ubiquitin K48C and NVA at pH 7.0.
FIG. 12B shows the ESI-MS spectrum of the raw and deconvoluted mass of product.

The reaction tube was irradiated under 365 nm UV for 2 h. The reaction product was analyzed by C18 analytical HPLC and confirmed by ESI or MALDI-TOF MS (See FIGS. 11 and 12). The protein remained soluble during the reaction period, indicating it stayed in its folded state.

FIG. 11A shows the C18 analytical HPLC profile of the thiol-ene coupling reaction between ubiquitin K48C and NVA at pH 4.0, where Peak a corresponds to ubiquitin K48C; and peak b corresponds to the acetylated product.

The MALDI-TOF MS spectrum of peak a is show in FIG. 11B, where [M+H]$^+$ found is 8541.78, and the calculated MW is 8539.88.

The MALDI-TOF MS spectrum of peak b is shown in FIG. 11C wherein the [M+H]$^+$ found is 8626.58, and the calculated MW is 8624.93. The HPLC was carried out under the following conditions: 0% to 30% in 15 min, then to 50% in 20 min of buffer B in buffer A.

FIG. 12A shows a C18 analytical HPLC profile of the thiol-ene coupling reaction between ubiquitin K48C and NVA at pH 7.0.

The raw and deconvoluted mass of product determined by ESI-MS is shown in FIG. 12B, where the MW found is 8624.0, and the calculated MW is 8624.93).

The HPLC was carried out under the following conditions: 0% to 30% in 15 min, then to 50% in 20 min of buffer B in buffer A.

This ubiquitin mutant contains a Cys residue at position 48. The protein (0.5 mM) was used in its native folded state for alkylation in the same reaction mixture at pH 4 or 7. The above MS analysis clearly showed an almost quantitative conversion, in 2 h, of the Cys residue to sLys(Ac) with the expected+85 Da MW for the alkylated product. The protein remained soluble during the reaction, suggesting that no denaturing was occurring and that the presence of 50 mM NVA and 5 mM VA-044 did not affect the structure of the folded protein. It is worth noticing that it would be difficult to use a semi-synthetic method to prepare such a modified protein since the modification site is in the middle of the sequence.

Figure 13:
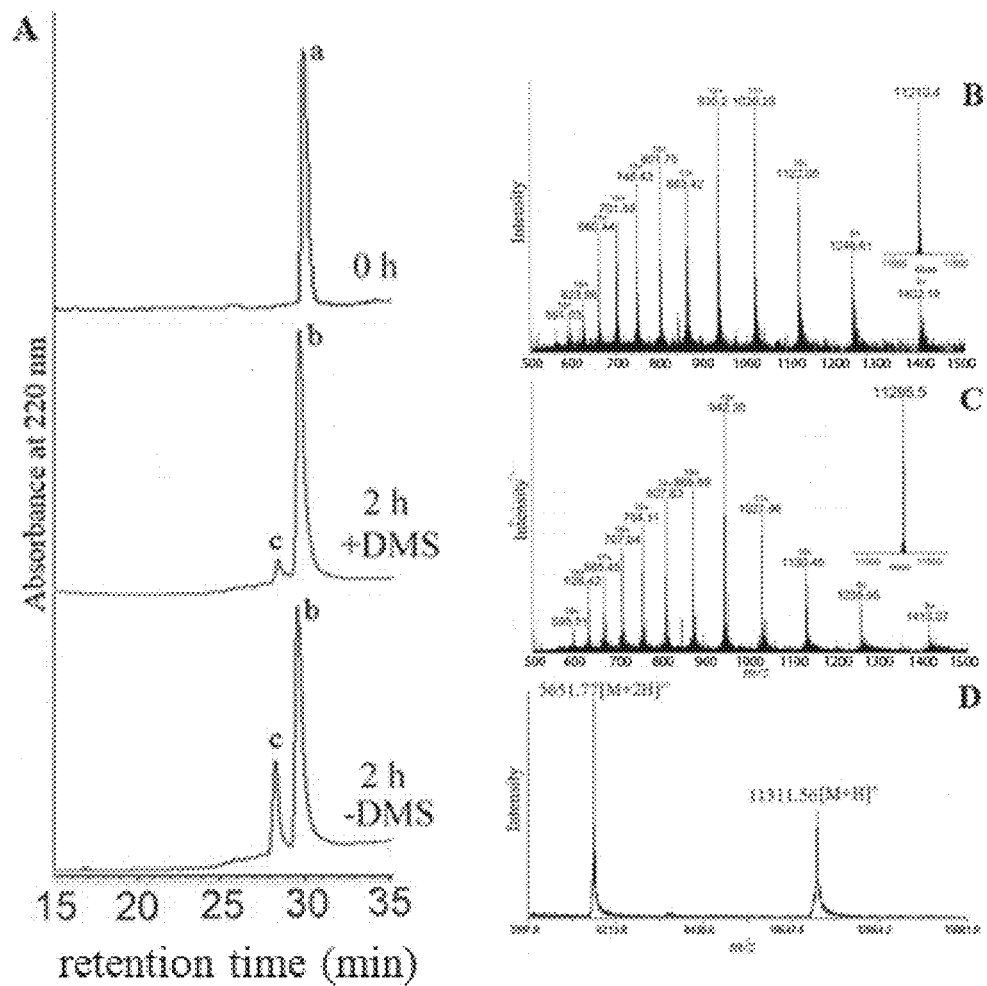
FIG. 13A shows a C4 semi-prep HPLC profile of the thiol-ene coupling reaction between H4 K16C and NVA at pH 4.0 with or without dimethyl sulfide. Peak a: H4 K16C; Peak b: expected product; Peak c: oxidation product.
FIG. 13B is an ESI-MS spectrum of the raw and deconvoluted mass of the starting material H4 K16C (shown in peak a).
FIG. 13C is an ESI-MS spectrum of the raw and deconvoluted mass of peak b.
FIG. 13D is a MALDI-TOF MS spectrum of peak c.
Figure 14:
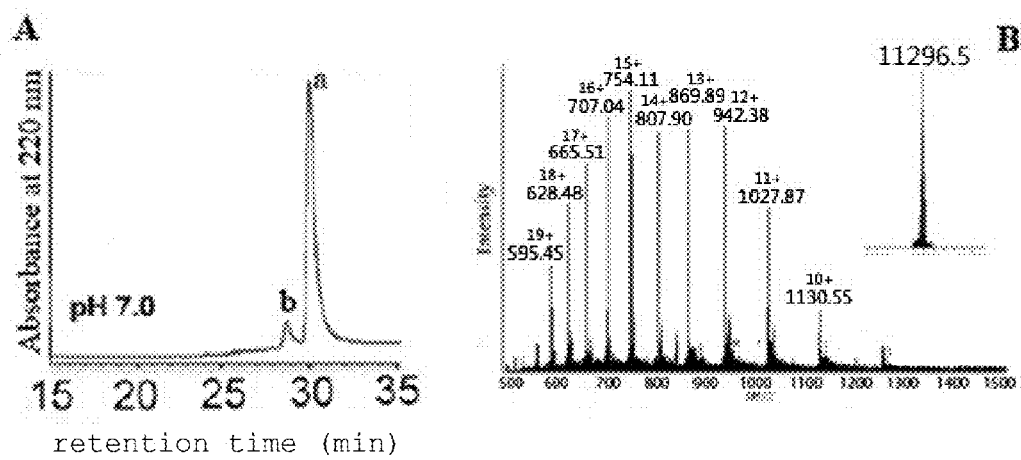

Two other proteins, histone H4 K16C and H3 K27C, were also modified with excellent results (see below). In these cases, 6 M Gdn-HCl was included in the alkylation reaction mixture. Interestingly, for the alkylation of H4 K16C at pH 4 or 7, in addition to the desired product, a side product was formed in significant amount (See below). The side product was more hydrophilic with a MW that was 16 Da higher than that of the expected acetyl-thialysine product. It appeared to result from oxidation of the thioether linkage to sulfoxide, and inclusion of dimethylsulfide in the reaction mixture minimized the formation of this side product to about 5% (See FIGS. 13 and 14).

No alkylation was detected when wild type H4 was subjected to the same treatment. From these results, it can be seen that this free radical thiol reaction can tolerate various reaction conditions, e.g., native or denatured buffers, to modify a protein.

Introduction of sLys(Ac) into Histone H4: Preparation of H4 $K_S16Ac$

The reaction was performed in the 0.2 M acetate buffer (pH 4.0 or pH 7.0) containing 6 M Guanidinium HCl. Dimethyl sulfide was added to minimize oxidation of the thioester linkage in this product.

The final concentrations of the reactants were as following:
H4 K16C: 1 mM.
NVA: 50 mM.
VA-044: 5 mM.
Glutathione: 15 mM.
Dimethyl sulfide: 100 mM.

The reaction tube was irradiated under 365 nm UV for 2 h. The reaction products were analyzed by C4 semi-prep HPLC and by ESI or MALDI-TOF MS (See FIGS. 13 and 14).

FIG. 13A is a C4 semi-prep HPLC profile of the thiol-ene coupling reaction between H4 K16C and NVA at pH 4.0 with or without dimethyl sulfide. Peak a shown in FIG. 13A corresponds to H4 K16C; whereas peak b corresponds to expected product; and peak c corresponds to the oxidation product.

The raw and deconvoluted mass of the starting material H4 K16C in peak a determined by ESI-MS is shown in FIG. 13B, wherein the MW found is 11210.4, and the calculated MW is 11211.16.

The raw and deconvoluted mass of peak b determined by ESI-MS is shown in FIG. 13C, where the MW found is 11295.5, and the calculated MW is 11296.21.

The MALDI-TOF MS spectrum of peak c is shown in FIG. 13D, where the $[M+H]^+$ found is 11311.56, and the calculated MW is 11312.2. The HPLC was performed under the following conditions: 0% to 40% in 20 min, then to 60% in 20 min of buffer B in buffer A.

FIG. 14A is a C4 semi-prep HPLC profile of the thiol-ene coupling reaction between H4 K16C and NVA at pH 7.0, where peak a corresponds to the expected product; and peak b corresponds to the oxidation product.

The raw and deconvoluted mass of peak a as determined by ESI-MS is shown in FIG. 14B, where the MW found is 11296.5, and the calculated MW is 11296.21. The HPLC was performed under the following conditions: 0% to 40% in 20 min, then to 60% in 20 min of buffer B in buffer A.

Introduction of sLys(Ac) into Histone H3: Preparation of H3 $K_S27Ac$

The reaction was performed in the 0.2 M acetate buffer (pH 4.0) containing 6 M Guanidinium HCl. The final concentrations of the reactants were as following:
H3 K27C: 1 mM.
NVA: 50 mM.
VA-044: 5 mM.
Glutathione: 15 mM.

Figure 15:
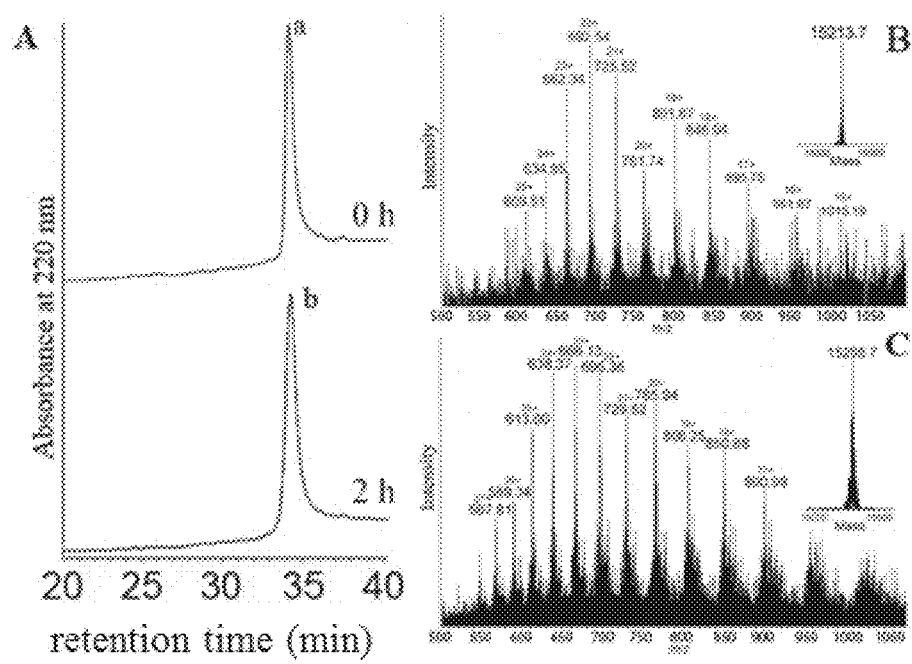

The reaction tube was irradiated under 365 nm for 2 h UV. The result was analyzed by C4 semi-prep HPLC and confirmed by ESI-MS (See FIG. 15).

The C4 semi-prep HPLC profile in FIG. 15A shows two peaks where peak a corresponds to the protein substrate H3 K27C and peak b corresponds to the acetylated product.

The ESI-MS spectrum of the raw and deconvoluted mass of peak a is provided in FIG. 15B, where the MW found is 15213.7, and the calculated MW is 15213.92.

The ESI-MS spectrum of the raw and deconvoluted mass of peak b is provided in FIG. 15C where the MW found is 15298.7, and the calculated MW is 15298.97. The HPLC were performed under the following conditions: 0% to 40% in 20 min, then to 60% in 20 min of buffer B in buffer A.

Table 3 below summarizes the reaction yields of the above described protein alkylation reactions in Examples 7 to 9.

TABLE 3

| Ex. | Substrate No. | Substrate | Amount (mM) | Reaction Time (h) | Yield (%) |
|---|---|---|---|---|---|
| 7 | 6 | Ubiquitin K48C | 0.5 | 2 | >95 |
| 8 | 7 | Histone H4 K16C | 1 | 2 | 90 |
| 9 | 8 | Histone H3 K27C | 1 | 2 | 90 |

From the above, it can be seen that apart from being effective on peptide substrates, the thiol-ene coupling reaction is also highly effective on protein substrates.

Example 10

In this example, the generated sLys(Ac) was shown to be a good functional mimic of the natural Lys(Ac) using Western blots.

3 μg of the control protein (H4 K16C) and H4 $K_S16Ac$ were dissolved respectively in loading buffer and run on 15% SDS-PAGE, then transferred onto a polyvinylidene difluoride membrane. Thereafter, 20 ml of TBST (50 mM Tris-HCl, 150 mM NaCl, 0.1% Tween 20, pH 7.4) containing 5% non-fat milk was added for 1 h. The membrane was then incubated in 20 ml TBST with 5% non-fat milk containing Histone H4 K16Ac antibody (1:1000 dilution) overnight at 4° C. The membrane was then washed with TBST 4 times and incubated in 20 ml TBST with 5% non-fat milk containing the anti-rabbit IgG peroxidase conjugate (1:5000 dilution) for 1 h at room temperature. After washing with TBST for 4 times, the proteins were visualized by chemiluminescence.

Figure 18:
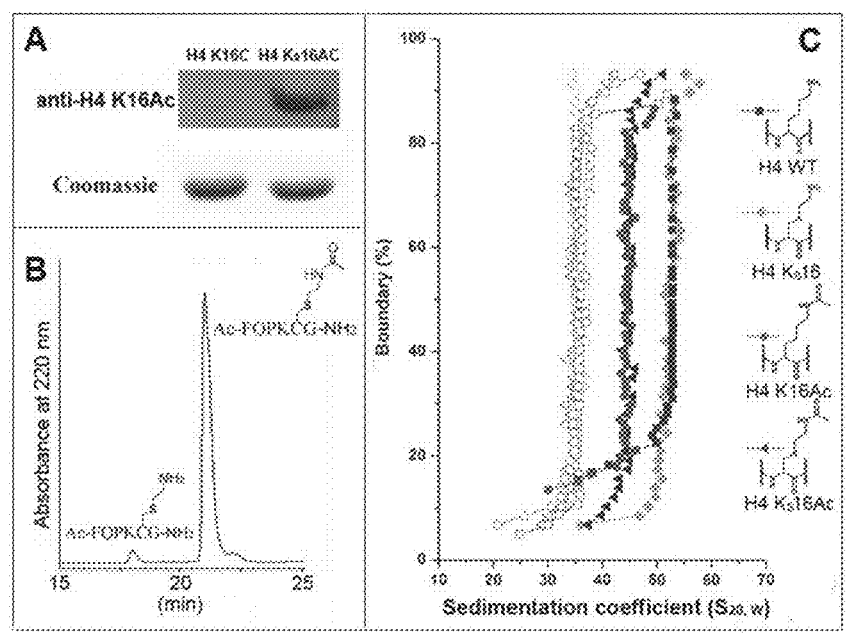
FIG. 18A show Western blots with anti-H4 K16Ac Ab on the H4 proteins: H4 K16C and H4 K$_S$16Ac.
FIG. 18B shows a deacetylation assay of Ac-FQPKKs(Ac)G (SEQ ID NO: 8) by SIRT2 after 16 h. The sequences, from left to right, correspond to SEQ ID NOs: 13 and 8.
FIG. 18C shows the effects of H4 K16 acetylation on nucleosome array folding as seen from sedimentation distributions of the nucleosome arrays before (no Mg$^{2+}$, open symbols) and after Mg$^{2+}$-induced folding (with 1.0 mM MgCl$_2$, solid symbols).

As seen in FIG. 18A, the histone protein H4 $K_S16Ac$ was recognized by a specific anti-H4 K16Ac antibody, as evidenced by the resultant darker stain on membrane. On the other hand, the unmodified H4 K16C was not recognized at all by the same antibody, as evidenced by the absence of a stain on the membrane.

Example 11

In this example, an enzymatic test was conducted to investigate whether the sLys(Ac) could be recognized by a histone deacetylase and used as a substrate for deacetylation.

Sirtuin-2 (SIRT2), a class III NAD-dependent deacetylase, was used for the deacetylation reaction of the alkylated acetyl-lysine analog of peptide 1 (Ac-FQPKK$_S$(Ac)G-NH$_2$) (SEQ ID NO: 8) and the native peptide 1 (Ac-FQPKK(Ac)G-NH$_2$) (SEQ ID NO: 7). The sequence of peptide 1 was based on residues 317-320 of protein p53 (i.e., Gln-Pro-Lys-Lys(Ac) (SEQ ID NO: 27)), which is the best deacetylase substrate for the SIRT2 enzyme, and the N-terminus was capped by an acetyl group to increase the hydrophobicity.

0.5 mM peptide and 0.1 mM NAD$^+$ were mixed in SIRT2 assay buffer (50 mM Tris, 137 mM NaCl, 2.7 mM KCl, 1 mM MgCl$_2$, 1 mg/ml BSA) and equilibrated at 37° C. for 10 min. The reaction was initiated by adding 0.1 mM SIRT2 enzyme (0.1 U/µl) at 37° C. and monitored by C18 analytical HPLC. It is to be noted that the deactylases were not very efficient in deacetylating synthetic peptide substrates and required relatively large amount of the enzyme and a long reaction time for the deacetylation reaction. The results showed that the deacetylation rate of the alkylated N-acetyl-thialysine peptide was about ⅓ of that on the control peptide containing the native N-acetyl-lysine.

Figure 16:
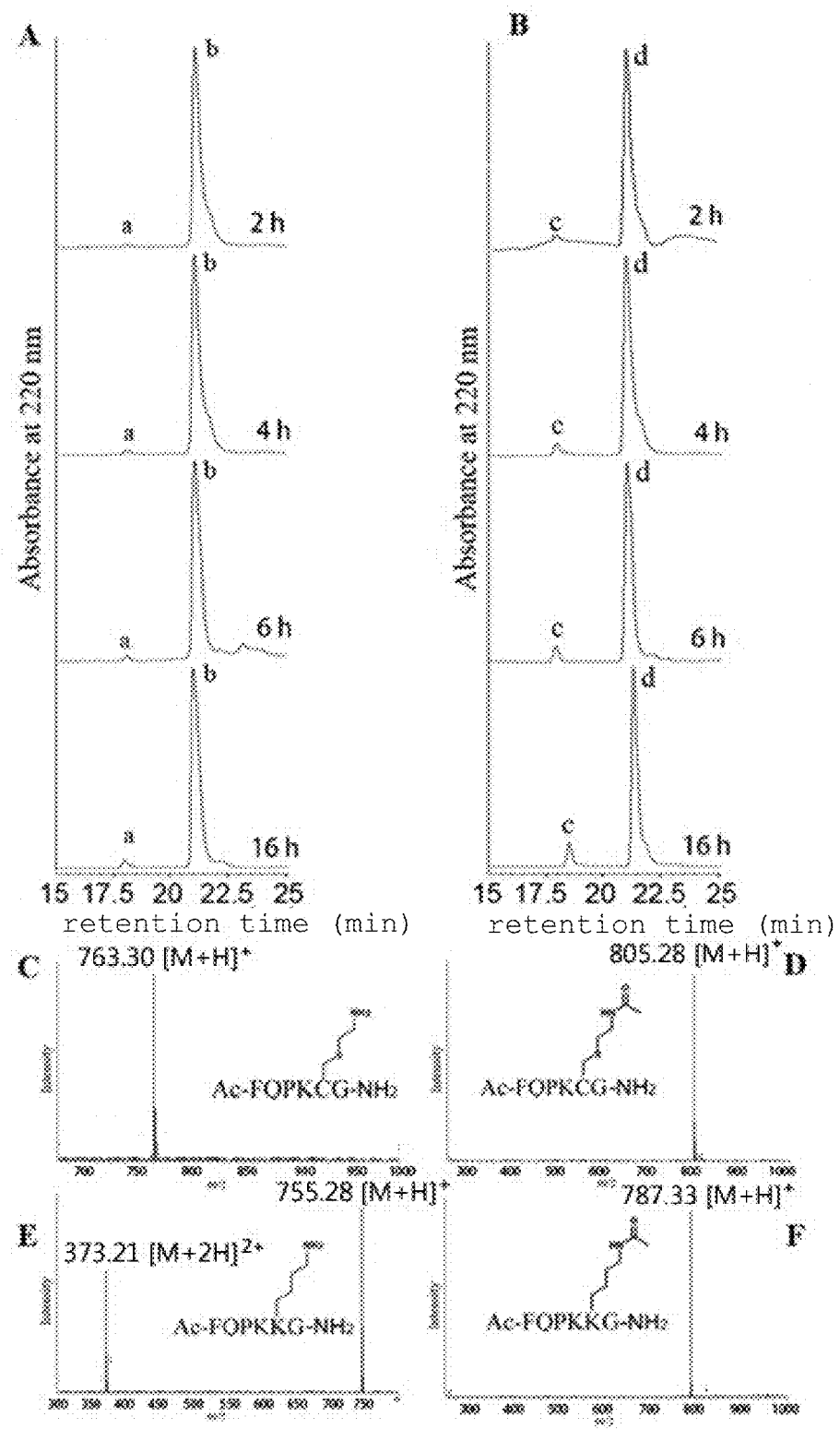
FIGS. 16A to 16F show the results of a SIRT2 mediated deacetylation assay.

The C18 analytical HPLC profile for Example 11 is shown in FIGS. 16A and 16B (or FIG. 18B). Specifically in FIG. 16A, the C18 analytical HPLC profile for the deacetylated product of peptide 1 with the installed acetyl-lysine analog in the SIRT2 assay is shown. In FIG. 16A, peak a denotes the deacetylated product, while peak b denotes the acetyl-lysine analog (Ac-FQPKK$_S$(Ac)G-NH$_2$ (SEQ ID NO: 8)). In FIG. 16B, the C18 analytical HPLC profile for the deacetylated product of the native K(Ac)-peptide substrate in the SIRT2 assay is shown. In FIG. 16B, peak c denotes the deacetylated product, while peak d denotes the native peptide substrate.

Peak a was further characterized by ESI-MS in FIG. 16C. In FIG. 16C, the mass spectrum of intensity versus the mass-to-charge ratio (m/z) of the deacetylated product of the acetyl-lysine analog is shown. The [M+H]$^+$ found had a m/z value of 763.30 and a molecular weight of 762.38.

Peak b was further characterized by ESI-MS in FIG. 16D. In FIG. 16D, the mass spectrum of intensity versus the mass-to-charge ratio (m/z) of the acetyl-lysine analog is shown. The [M+H]$^+$ found had a m/z value of 805.28 and a molecular weight of 804.39.

Peak c was further characterized by ESI-MS in FIG. 16E. In FIG. 16E, the mass spectrum of intensity versus the mass-to-charge ratio (m/z) of the deacetylated product of the native K(Ac)-peptide substrate is shown. The [M+H]$^+$ found had a m/z value of 745.28 and a molecular weight of 744.43.

Peak d was further characterized by ESI-MS in FIG. 16F. In FIG. 16F, the mass spectrum of intensity versus the mass-to-charge ratio (m/z) of the native K(Ac)-peptide substrate is shown. The [M+H]$^+$ found had a m/z value of 787.33 and a molecular weight of 786.44.

The HPLC conditions used in Example 11 were 0% to 30% of buffer B in buffer A in 30 min.

It can thus be concluded that the sLys(Ac) residue in the alkylated peptide 1 was susceptible to enzymatic deacetylation, albeit to a lesser degree, compared to its native counterpart. This is evidenced by the smaller peak a as compared to peak c.

Example 12

Preparation of H4 $K_S16$

In this example, H4 $K_S16$ was synthesized using the classic aminoethylation reaction.

H4 K16C (0.5 mM) was dissolved in the 1 M HEPES [4-(2-hydroxyethyl)-1-piperazineethanesulfonic acid] buffer (pH 7.8, 6 M Gdn HCl, 5 mM D/L methionine, 20 mM dithiothreitol (DTT)) containing 2-bromoethylamine hydrobromide (160 mM). After an 11 h reaction at room temperature in the dark, the alkylated protein was dialyzed to ddH$_2$O followed by lyophilization. The reaction product was analyzed by ESI-MS and is shown in FIG. 17.

Figure 17:
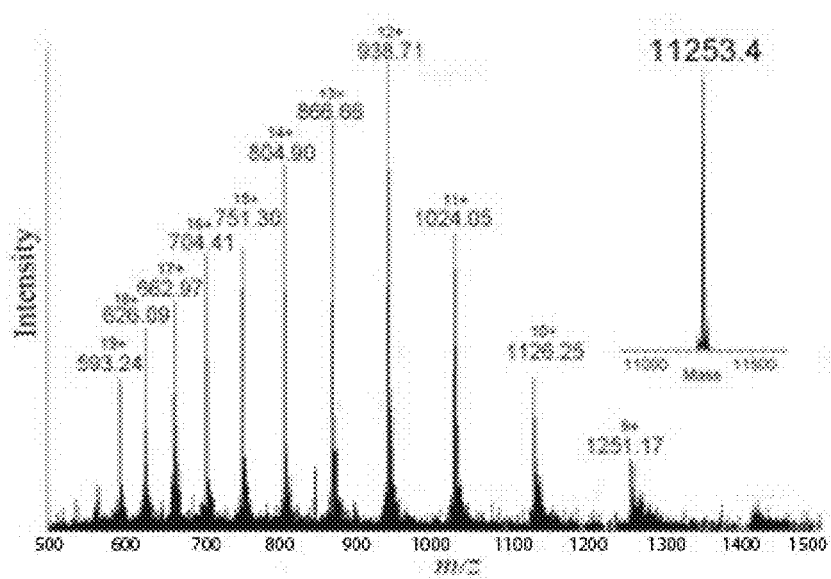
FIG. 17 is an ESI-MS spectrum of the raw and deconvoluted mass of the alkylated product H4 K$_S$16.

In FIG. 17, the raw spectrum and deconvoluted mass of the alkylated product (H4 $K_S16$) as determined by ESI-MS had a molecular weight of 11253.4, while the molecular weight calculated was 11254.2.

Example 13

Acetylation of Lys16 in histone H4 is known to inhibit the folding of nucleosome arrays and hence the formation of the compact 30-nm chromatin fiber. H4 $K_S16Ac$ and three other control H4 proteins (H4 K16Ac, H4$K_S16$ and H4-WT, described below) were incorporated respectively, together with H3, H2A and H2B, into histone octamers.

H4 K16Ac was prepared using a semi-synthetic approach and H4 $K_S16$ was synthesized in Example 12 by alkylating H4 C16 with 2-bromoethylamine. The four different octamers were then individually combined with the 12-177-601 DNA to assemble into the 12-nucleosome arrays.

Using analytical ultracentrifugation, it was demonstrated that the $K_S16Ac$ produced an identical effect as the native K16Ac in abolishing Mg$^{2+}$-induced folding of the reconstituted nucleosome array, as seen in FIG. 18C.

The AUC data clearly showed that, in the presence of 1 mM MgCl$_2$, the nucleosome array containing wild-type H4 or its equivalent H4 $K_S16$ folded into a significantly more compact state (sedimentation coefficient $S_{20° C., w}$=52-53S) than did the K16Ac and $K_S16Ac$ arrays ($S_{20° C., w}$=44-45S). Remarkably, these results prove not only the functional equivalency between sLys(Ac) and Lys(Ac), but also the functional equivalency between sLys and Lys.

Nucleosomal Array Reconstitution:

Plasmid containing the 12-177-601 DNA was transformed and amplified in HB101 cell. The plasmid was extracted as described in Korolev et al, *Biophys. J.* 2010, 99, 1865-1905.

RNA and protein impurities were removed by gel filtration on a Sepharose 6 column with the use of TES2000 buffer. After excision with EcoRV, the 12-177-601 DNA was separated from short plasmid fragment by polyethylene glycol (PEG 6000). Finally 12-177-601 DNA was purified on a Sephacryl SF1000 column with TES100 buffer.

Wild type *Xenopus laevis* histones H2A, H2B, H3, and H4 were individually over-expressed in BL21 (DE3) pLysS cell in presence of ampicillin and chloramphenicol. Each histone was purified by gel filtration on Sephacryl S-200 column and subsequently on a Resource S cation exchange column. The H4 K16Ac was prepared by chemical semi-synthesis described in Allahverdi et al, *Nucleic Acids. Res.,* 2011, 39, 1680-1691.

The histone octamer was formed using a molar ratio of 1:1:1.2:1.2 for H2A, H2B, H3, and H4. The histone octamer was purified on a Sephacryl S-200 gel filtration column.

The nucleosome array was reconstituted by step-wise dialysis using the histone octamer and 12-177-601 DNA as described in Rorigo et al, *J. Mol. Biol.,* 2003, 327, 85-96 and T. Schalch, *The 30-nm chromatin fiber. In vitro reconstitution and structural analysis.* PhD Thesis. 2004, Swiss Federal Institute of Technology, Zurich. e-collection.library.ethz.ch/eserv/eth:27516/eth-27516-02.pdf.

To prevent excessive binding of the histone to the DNA, 0.5 molecule of competitor Core Length DNA (150-bp) per one array was added to the reconstitution mixture. The exact amount of histone octamer to 12-177-601 DNA to get the stoichiometry of 12:1 was determined empirically in small scale preparations using different ratios of histone octamer to the DNA template. The reconstituted arrays were purified as described above. Purified array material and also the respective digests by ScaI were checked on 5% poly acrylamide gel electrophoresis (PAGE) to verify the quality of the nucleosomal arrays.

Analytical Ultracentrifugation

Sedimentation velocity experiments were carried out on a Beckman XL-I analytical ultracentrifuge with AN-50T rotor and monochrome scanner. The stock solution of array was diluted in TEK buffer to get $A259=0.8$ cm$^{-1}$ (DNA concentration Cp=121 µM).

The sample and reference (TEK buffer+salt at same concentration as in the sample) were loaded into the 12 mm double channel cells and equilibrated under vacuum for 30 min at 3000 rpm and 20° C. Data measurement and analyses were carried out following methods described in Korolev et al and Allahverdi et al described above.

Table 4 provides values of $S_{20°\ C,w} \pm SD$ of nucleosome arrays in the presence of different concentrations of Mg$^{2+}$.

TABLE 4

| Mg2+ concentration | Array | | | |
|---|---|---|---|---|
| | H4 WT | H4 K$_s$16 | H4 K16AC | H4 K$_s$16Ac |
| 0.0 mM | 35.4 ± 0.27 | 35.2 ± 0.68 | 36.2 ± 0.93 | 34.8 ± 0.77 |
| 0.4 mM | 42.5 ± 0.3 | 40.7 ± 0.42 | 40 ± 1.32 | 41.6 ± 0.76 |
| 0.8 mM | 48.5 ± 0.25 | 48.9 ± 0.79 | 42.9 ± 0.61 | 43.3 ± 0.59 |
| 1.0 mM | 52.7 ± 0.4 | 52.3 ± 1.03 | 44.4 ± 0.6 | 44.7 ± 0.56 |

Example 14

The reaction with vinyl acetate was also successful. The reaction with methyl vinyl ether and di(ethylene glycol) vinyl ether obtained similar results. The product of the reaction on the Cys residue of a target molecule with vinyl acetate is also a mimic of Lys(Ac). But more importantly, the reaction with polyethylene glycol) vinyl ether is a very useful method for PEGylation of peptides and proteins.

PEGylation is being increasingly used for peptide/protein modification as a way to prolong the half-life of therapeutic peptides and proteins. Several PEGylated peptides and proteins (e.g., PEG-interferon alpha, PEG-G-CSF) are already on the market.

An experiment was carried out on one exemplary peptide (Peptide 1 in Table 1 above: Ac-Phe-Gln-Pro-Lys-Cys-Gly-amide (SEQ ID NO: 1)). The reaction was conducted in the acetate buffer (pH 4) containing 5 mM of peptide 1, 100 mM vinyl acetate, 5 mM VA-044 and 15 mM glutathione. After 2 h UV (365 nm) irradiation at room temperature, >90% alkylation product was obtained ([M+H]$^+$ found 805.2).

Example 15

Alkylation with N-vinylpropionylamide or N-vinylbutyramide

Alkylation of a Cys residue with N-vinylpropionylamide or N-butyramide generates a mimic of N$^\epsilon$-propionyl-Lys or N$^\epsilon$-butyryl-Lys residue, respectively. The mechanism of reaction is as provided in Scheme V below:

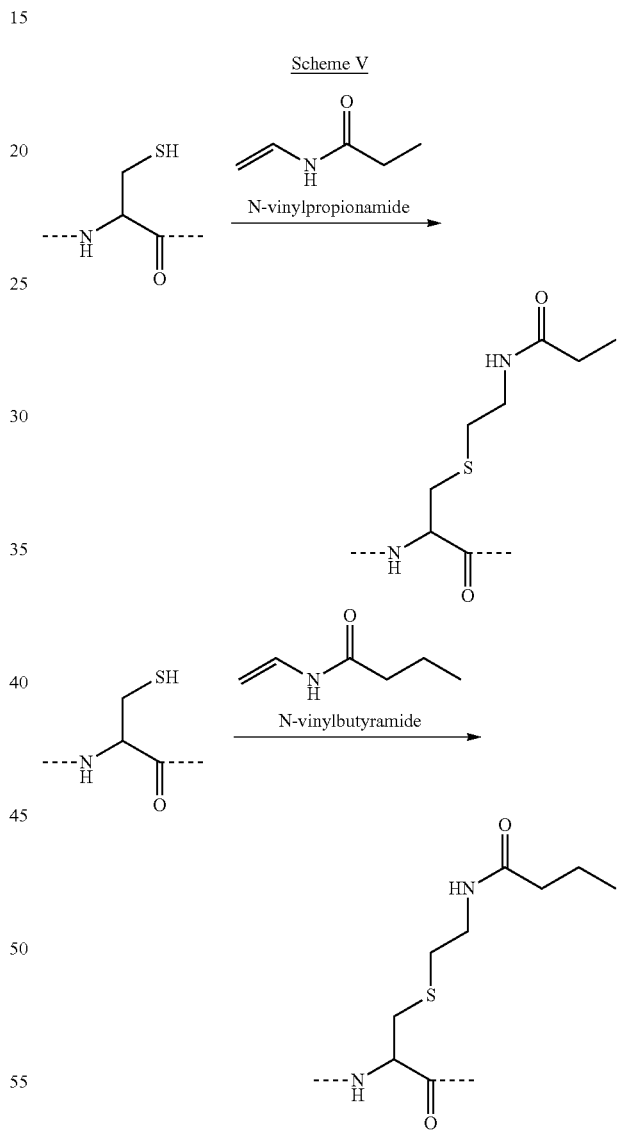

Scheme V

Methods

Peptide 1 from Table 1 was used as the substrate. All the reactants were dissolved in the 0.2 M acetate buffer (pH 4.0) as indicated above and the final concentrations were as follows:

Peptide 1: 5 mM
N-vinylpropionamide or N-vinylbutyramide: 50 mM
VA-044: 5 mM
Glutathione (reduced form): 15 mM The reaction tube was irradiated under 365 nm UV for 1 h at room temperature. The reaction products were analyzed by C18 analytical HPLC and confirmed by ESI or MALDI-TOF MS. MS analysis was done on either desalted samples (using a C18 zip-tip) or on HPLC-purified fractions.

Results

Figure 19:
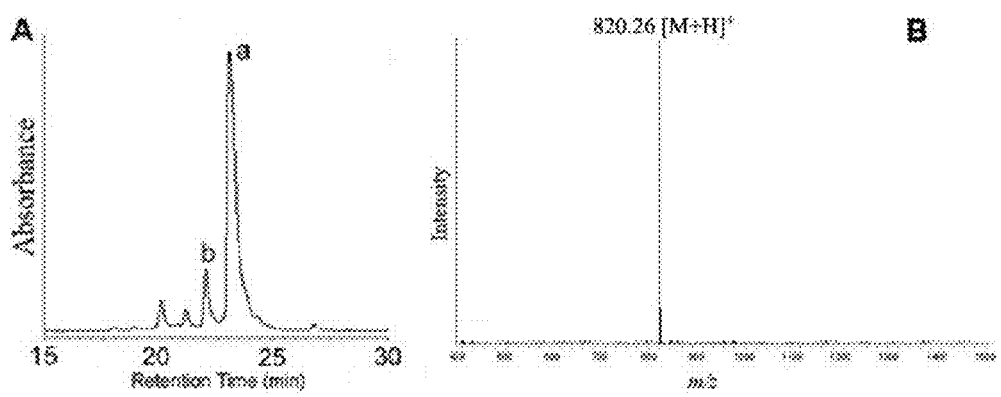
Figure 20:
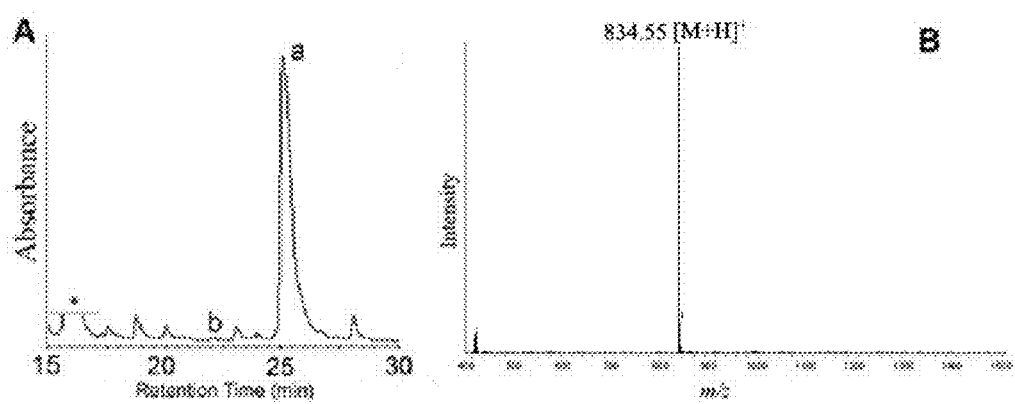

With reference to FIGS. 19 and 20, it can be seen that the reaction of peptide 1 with N-vinylpropionamide or N-vinylbutyramide was similar to that with NVA. The reaction was clean and efficient with a yield of over 85% after 1 h. No telomerization side products were detected.

Specifically, FIG. 19A shows the C18 analytical HPLC profile of the thiol-ene coupling reaction between peptide 1 and N-vinylpropionamide, where Peak a corresponds to the product; Peak b corresponds to peptide 1. FIG. 19B shows the ESI-MS of peak a where the [M+H]$^+$ found was 820.26, and the calculated MW was 819.52. The HPLC was performed under the following conditions: 0% to 40% of buffer B in buffer A in 40 min.

FIG. 20A shows the C18 analytical HPLC profile of the thiol-ene coupling reaction between peptide 1 and N-vinylbutyramide, where Peak a corresponds to the product; Peak b corresponds to peptide 1. FIG. 20B shows an ESI-MS of peak a where the [M+H]$^+$ found is 834.55, and the calculated MW is 833.67. The HPLC was performed under the following conditions: 0% to 40% of buffer B in buffer A in 40 min.

Example 16

Comparative Study of the Alkylation Reaction with NVA, Vinyl Acetate, N-allylacetate or N-methyl-N-vinylacetate Several ene reagents (alkylating reagents), vinyl acetate, N-allylacetate and N-methyl-N-vinylacetate, were compared with NVA in the reaction with Cys to generate other N$^\epsilon$-acetyl-lysine analogues by the thiol-ene coupling method. Their respective reaction mechanisms are provided in Scheme VI below.

Although these analogues are structurally similar, they differ from one another in electrosteric properties which may result in subtle differences in functions and therefore may be useful for better understanding the effects of protein modifications by the acetyl group.

Scheme VI

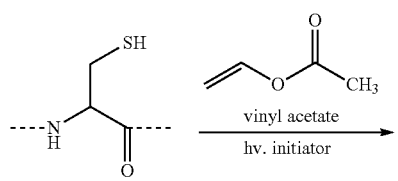
vinyl acetate
hv. initiator

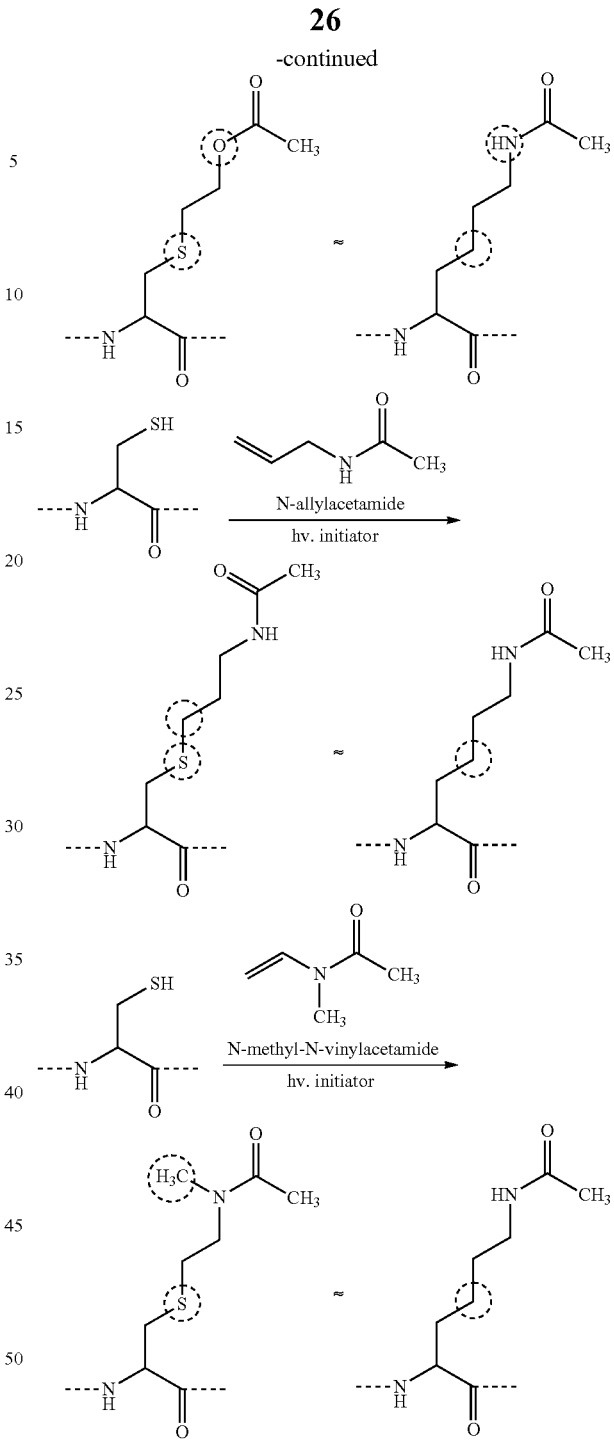

Methods
For the site-specific installation of the acetyl-lysine analogs shown in Scheme VI, a model peptide (peptide 1) was modified by the thiol-ene coupling reaction. All the reactants were dissolved in the 0.2 M acetate buffer (pH 4.0) as indicated, and the final concentrations were as follows:
Peptide 1: 5 mM
vinyl acetate, or N-allylacetamide, or N-methyl-N-vinylacetamide: 50 mM
VA-044: 5 mM
Glutathione (reduced form): 15 mM
The reaction tube was irradiated under 365 nm UV for 1 h at room temperature. The reaction products were analyzed by C18 analytical HPLC and confirmed by ESI or MALDI-TOF MS. MS analysis was done on either desalted samples (using a C18 zip-tip) or on HPLC-purified fractions.

Figure 21:
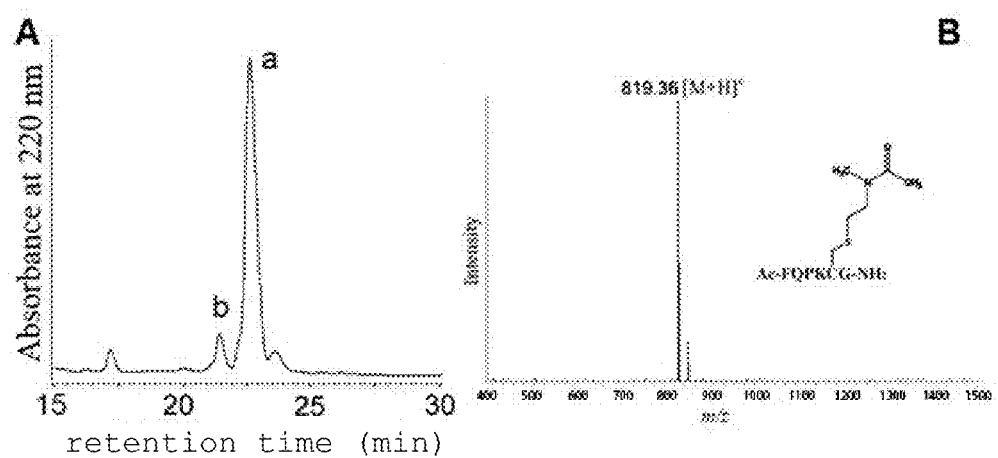
FIG. 21A shows a C18 analytical HPLC profile of the thiol-ene coupling reaction between peptide 1 and N-methyl-N-vinylacetamide. Peak a: product; Peak b: peptide 1.
FIG. 21B shows an ESI-MS of peak a. The sequence corresponds to SEQ ID NO: 15.
Figure 22:
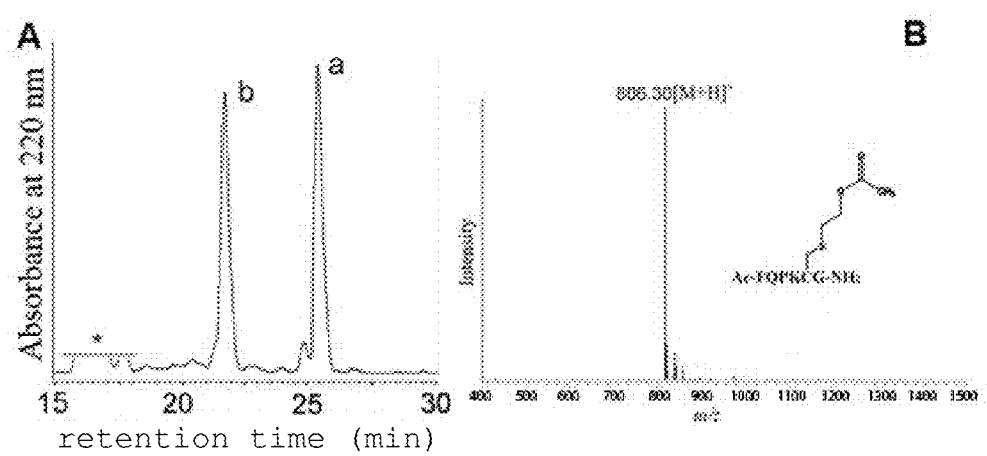
FIG. 22A shows a C18 analytical HPLC profile of the thiol-ene coupling reaction between peptide 1 and vinyl acetate. Peak a: product; Peak b: peptide 1; Peak *: unidentified peak.
FIG. 22B shows an ESI-MS of peak a. The sequence corresponds to SEQ ID NO: 16.
Figure 23:
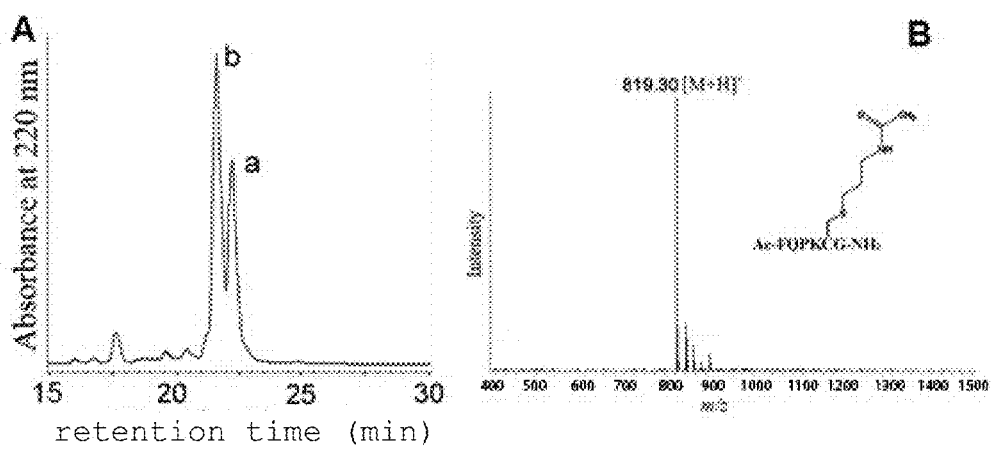
FIG. 23A shows a C18 analytical HPLC profile of the thiol-ene coupling reaction between peptide 1 and N-allylacetamide. Peak a: product; Peak b: peptide 1.
FIG. 23B shows an ESI-MS of peak a. The sequence corresponds to SEQ ID NO: 17.

Peptide 1 was treated in a similar way with vinyl acetate, N-allylacetamide, and N-methyl-N-vinylacetamide respectively to generate different acetyl-lysine analogues. The experimental results are provided in FIGS. 21-23.

A notable distinction from the reaction with NVA was that no telomerization side products were detected. Although all these alkylating agents contain a C=C double bond, their reactivities appeared to be different. In particular, these alkylating agents appeared to be less reactive than NVA.

Table 5 lists the yields at 1 h of the reactions with the different alkylating agents used in this Example. As seen from Table 5, the reactivity order is: N-vinylacetamide>N-methyl-N-vinylacetamide>vinyl acetate>N-allylacetamide. In particular, while a yield of >95% was obtained with NVA at 1 h, the respective yields obtained with N-methyl-N-vinylacetamide, vinyl acetate and N-allylacetamide were about 79%, 51% and 38%. This may have resulted from the different stabilities of the radical intermediates or from the different steric effects of these alkylating agents. Notably, all the reactions were very clean (FIGS. 21-23) and proceeded to completion with prolonged time (data not shown).

In particular, FIG. 21A shows a C18 analytical HPLC profile of the thiol-ene coupling reaction between peptide 1 and N-methyl-N-vinylacetamide, wherein Peak a corresponds to the product; and Peak b corresponds to peptide 1. FIG. 21B shows the ESI-MS of peak a, where the $[M+H]^+$ found is 819.36, whereas the calculated MW is 818.40. The HPLC was performed under the following conditions: 0% to 40% of buffer B in buffer A in 40 min.

FIG. 22A shows a C18 analytical HPLC profile of the thiol-ene coupling reaction between peptide 1 and vinyl acetate, wherein Peak a corresponds to the product; and Peak b corresponds to peptide 1. FIG. 22B shows the ESI-MS of peak a, where the $[M+H]^+$ found is 806.30, whereas the calculated MW is 805.37. The HPLC was performed under the following conditions: 0% to 40% of buffer B in buffer A in 40 min.

FIG. 23A shows a C18 analytical HPLC profile of the thiol-ene coupling reaction between peptide 1 and N-allylacetamide, wherein Peak a corresponds to the product; and Peak b corresponds to peptide 1. FIG. 23B shows the ESI-MS of peak a, where the $[M+H]^+$ found is 819.30, whereas the calculated MW is 818.40. The HPLC was performed under the following conditions: 0% to 40% of buffer B in buffer A in 40 min.

TABLE 5

Comparison of different ene reagents in thio-ene coupling reaction

| Peptide 1 | Alkylating agent | Product | Yield (1 h) (%) |
|---|---|---|---|
| Ac-FQPKCG (SEQ ID NO: 1) | N-vinylacetamide | | >95 |
| Ac-FQPKCG (SEQ ID NO: 1) | N-methyl-N-vinylacetamide | | 78.7 |

TABLE 5-continued

Comparison of different ene reagents in thio-ene coupling reaction

| Peptide 1 | Alkylating agent | Product | Yield (1 h) (%) |
|---|---|---|---|
| Ac-FQPKCG (SEQ ID NO: 1) | vinyl acetate | | 50.9 |
| Ac-FQPKCG (SEQ ID NO: 1) | N-allylacetamide | | 38.3 |

Example 17

Alkylation with N-vinyl-peptidylamide or N-vinyl-proteinylamide

In this Example, the same thiol-ene coupling reaction is carried out but with a peptidylamide and proteinylamide alkylating agent. In these two cases, the -ene compound has a large acyl group, i.e., the peptidyl or proteinyl group (See Scheme VII below). The thiol compound can be a small organic thiol compound, a peptide/protein containing Cys residue(s) or a thiol-functionalized polymer (e.g., PEG).

Scheme VII

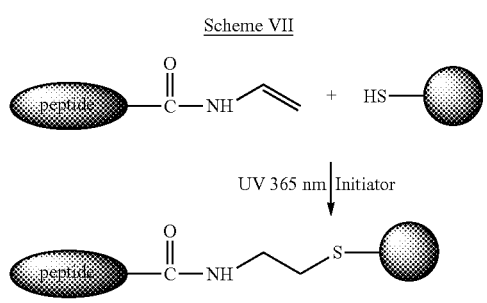

The initial step is to prepare a peptide or protein with a C-terminal vinyl (or allyl) amide. The present inventors have developed an indirect method for this synthesis.

A peptide or protein thioester is first prepared chemically or biosynthetically, and is then reacted with N-vinyl-glycylamide (i.e., 2-amino-N-vinylacetamide) in the presence of silver ions (See Scheme VIII below). This allows the introduction of the N-vinyl group onto the C-terminus of the peptide with the extension of one amino acid (Gly in this case). A peptide thioester can be prepared by the solid phase peptide synthesis technique and a large peptide or protein thioester can be prepared by using the intein-catalyzed protein splicing technique.

Scheme VIII

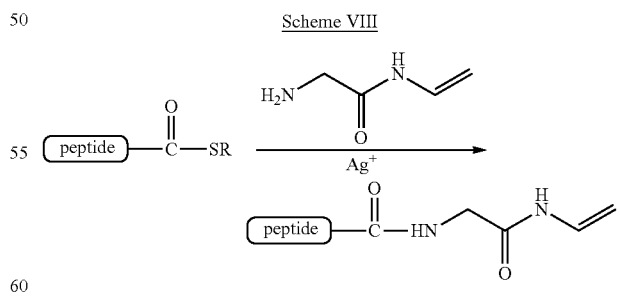

Using this method, a small peptide (RLYRAG (SEQ ID NO: 28)) and a protein (ubiquitin) were prepared, each containing the C-terminal N-vinyl amide (See Scheme IX below). Specifically, the peptide N-vinyl amide was prepared from RLYRA-COSR (SEQ ID NO: 29) and the ubiquitinyl N-vinylamide was prepared from the Ub(1-75)-COSR.

Scheme IX

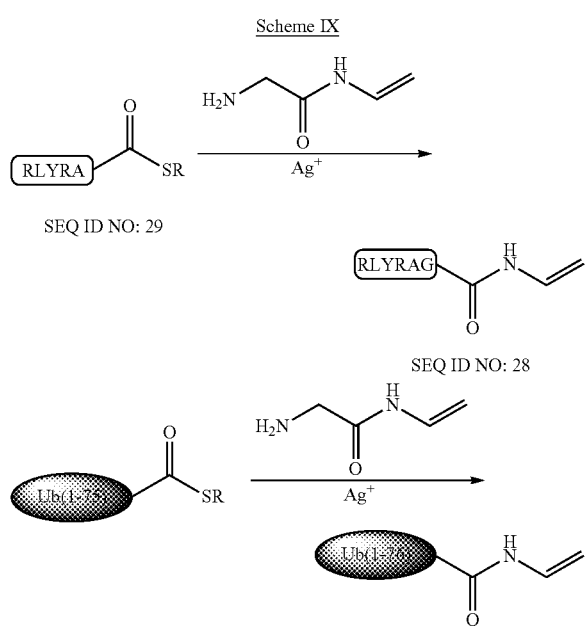

A small thiol compound, methyl mercaptoacetate, was used to react with the peptide RLYRAG-vinyl amide (SEQ ID NO: 18) in the thiol-ene coupling reaction. It was found that the vinyl group on the C-terminal amide of the peptide was much less reactive than in NVA. When VA-044 was used as the radical initiator, the reaction could only take place at elevated temperature (at 60° C. or higher) with only a modest yield.

It was further found that a different photoinitiator, lithium phenyl-2,4,6-trimethylbenzoylphosphinate (LAP), was better than VA-044 in promoting the thiol-ene radical reaction in this case. At 50° C., over 70% of reaction product was obtained after 2 h reaction with LAP as the photoinitiator.

Figure 24:
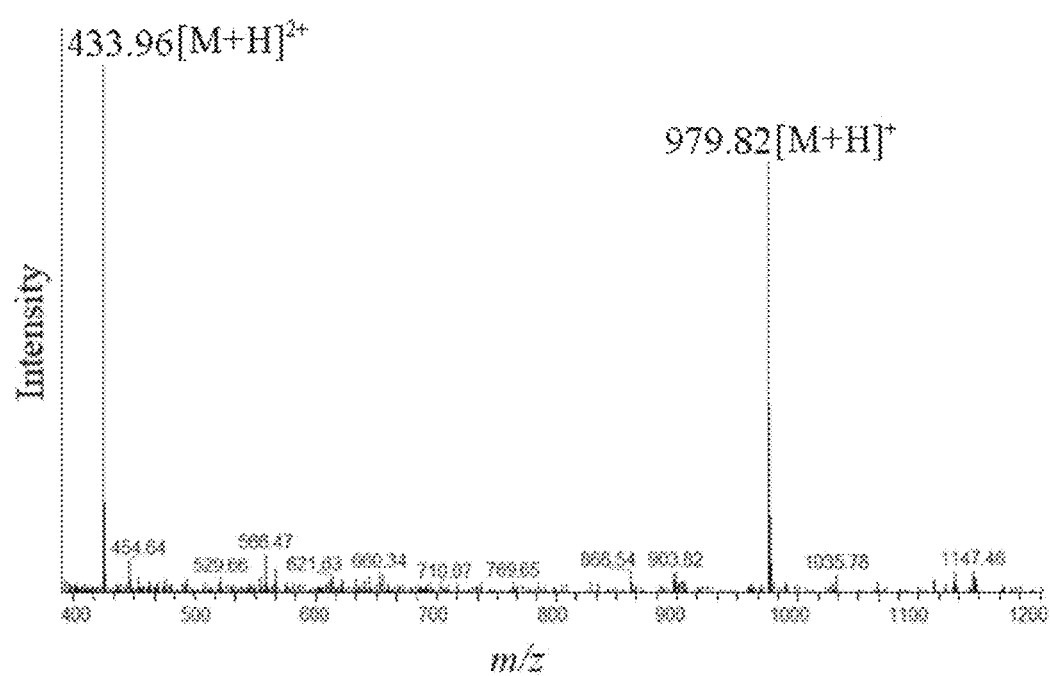
FIG. 24 shows an ESI-MS of the isolated product formed from the thiol-ene coupling reaction between RLYRAG-vinyl amide (SEQ ID NO: 18) and methyl mercaptoacetate.

FIG. 24 shows the EMI-MS of the isolated product formed from the thiol-ene coupling reaction between RLYRAG-vinyl amide (SEQ ID NO: 18) and methyl mercaptoacetate, wherein the [M+H]$^+$ found: was 972.82 (+113 TFA adduct, because of the highly basic nature of the peptide) and the calculated MW: was 894.88.

This initiator (LAP) was also used for the reaction of the ubiquitin-vinyl amide. A relatively large thiol substrate Ubi-K48C was used, which is monoubiquitin in which Lys48 was mutated to Cys. After 1 h reaction at 50° C., the diubiquitin product was formed at about 35-40% as analyzed from SDS-PAGE gel.
Methods
Experimental Procedures for Peptide RLYRAG-vinyl amide (SEQ ID NO: 18)
Preparation of Peptide RLYRAG-vinyl amide (SEQ ID NO: 18)

The thioester peptide RLYRA-COSR (SEQ ID NO: 29) was reacted with 2-amino-N-vinylacetamide in the presence of silver ions at room temperature. All the reagents were dissolved in DMSO and the reaction conditions were as follows:
RLYRA-COSR (SEQ ID NO: 29): 5 mM
2-amino-N-vinylacetamide: 100 mM
AgNO$_3$: 100 mM
After 16 h, the product was purified by C18 semi HPLC followed by lyophilization.

Thiol-ene Coupling Reaction Between RLYRAG-vinyl amide (SEQ ID NO: 18) and methyl mercaptoacetate The purified RLYRAG-vinyl amide (SEQ ID NO: 18) was thereafter reacted with methyl mercaptoacetate by the thiol-ene coupling reaction. The reaction was performed in 0.2 M acetate buffer (pH 4 or 5).

The final concentrations of the reactants were as follows:
RLYRAG-vinyl amide (SEQ ID NO: 18): 10 mM
methyl mercaptoacetate: 40 mM
LAP: 5 mM The reaction tube was irradiated under 365 nm UV at 50° C. for 2 h. The reaction product was purified by HPLC and confirmed by ESI-MS (See FIG. 24).
2) Experimental Procedures for N-vinyl-ubiquitinylamide (Ubi-vinyl amide)
Preparation of Ubi (1-75)-COSR The human ubiquitin gene was amplified by PCR using the primers:

```
                                    (SEQ ID NO: 30)
Ubi75_F:
5'-GGTGGTCATATGCAGATCTTTGTGAAG-3';
and (SEQ ID NO: 31)
Ubi75_R:
5'-CTGGTCAGGTGGGATACCCTCCTTGTCTTGAATTTTG-3'.
```

The PCR product was purified and ligated into the T-easy vector (Promega). After digestion with NdeI and SapI restriction enzymes, the product was purified and ligated into the identically digested pTYB1 vector (New England Biolabs). Then the correct insert was confirmed by sequencing.

The plasmid pUbi 75aa-TYB1 was transformed into E. coli BL21(DE3) cells. The cells were grown in LB medium (containing 100 µg/ml Ampicillin) at 37° C. to an OD600 of 0.6-0.8. The desired protein was induced by 50 µM IPTG at 15° C. for 18 h. After centrifuge at 6000 rpm for 10 mins, cell pellets from 1 liter of cells were resuspended in 50 ml lysis buffer (50 mM HEPES, 500 mM NaCl, 1 mM beta-mercaptoethanol, pH 7.5). Cells were then broken by sonication and debris removed by centrifugation at 20,000 g for 30 min. The supernatants are then mixed with pre-equilibrated 3 ml chitin beads (New England Biolabs) at 4° C. for 2 h. The beads were then poured into a column and washed with 40 ml lysis buffer. The fusion protein was cleaved by adding 4 ml lysis buffer containing 100 mM 2-mercaptoethanesulfonic acid (ME-SNA) and incubating at 37° C. overnight. The Ubi(1-75) thioester was eluted by 10 ml lysis buffer. Affinity binding, cleavage and purification were monitored by SDS-PAGE and HPLC. The purified Ubi(1-75)-COSR was dried by lyophilization.
Preparation of Ubi-vinyl amide The purified Ubi(1-75)-COSR was reacted with 2-amino-N-vinylacetamide to generate the Ubi-vinyl amide. All the reagents were dissolved in DMSO and the reaction conditions were as follows:
Ubi(1-75)-COSR: 2 mM
2-amino-N-vinylacetamide: 100 mM
AgNO$_3$: 100 mM
After 16 h, the product was purified by C4 semi HPLC followed by lyophilization.
Preparation of Ubi-K48C K48C point mutation was introduced to ubiquitin gene by QuikChange™ site-directed mutagenesis kit (Stratagene) with the primers:

(SEQ ID NO: 19)
Ubi K48C F:
5'-GTCTGATATTTGCCGGCTGTCAGCTGGAGGATGGCCG-3';
and (SEQ ID NO: 20)
Ubi K48C R:
5'-CGGCCATCCTCCAGCTGACAGCCGGCAAATATCAGAC-3'.

The plasmid containing ubiquitin K48C gene was transformed into BL21 (DE3) cells. The cells were grown in 1 L LB media containing ampicillin to OD600 of 0.6 and induced by a final concentration of 0.5 mM IPTG for 4 h at 37° C. After centrifugation at 6000 rpm for 10 min at 4° C., cells were resuspended in 50 ml lysis buffer (50 mM Tris-HCl, 100 mM NaCl, 1 mM DTT, pH 7.5) and broken by microfluidization (Microfluidics, Newton, USA). After centrifugation at 25,000 g for 30 min at 4° C., 70% perchloric acid was added to the supernatant at a ratio of 350 µl to 50 ml lysis buffer. The mixture was stirred for 10 min and centrifuged at 25,000 g for 30 min at 4° C. The supernatant was filtered with 0.2 µm filter and dialyzed with 3.5 KDa cut-off dialysis tubing against 50 mM ammonium acetate buffer (pH 4.5 with 1 mM DTT).

After filtration, the proteins were purified with a HiTrap™ SP FF 5 ml FPLC column (GE Healthcare Life Sciences). It was eluted with a linear gradient from 0% to 100% FPLC buffer B (50 mM ammonium acetate, pH 4.5, 1 mM DTT, 0.5 M NaCl) in buffer A (50 mM ammonium acetate, pH 4.5, 1 mM DTT) in 120 min at a flowrate 0.5 ml/min.

Usually the ubiquitin would be eluted at around 240 mM NaCl. After FPLC purification, the proteins were dialyzed to ddH$_2$O followed by lyophilization.

Synthesis of di-ubiquitin by thiol-ene Coupling Reaction

The purified Ubi-vinyl amide was reacted with Ubi-K48C to generate di-Ubi by thiol-ene coupling reaction. The reaction was performed in the 0.2 M acetate buffer (pH 5.0) containing 6 M Guanidinium HCl. The final concentrations of the reactants were as follows:

Ubi-vinyl amide: 2 mM
Ubi-K48C: 2 mM
LAP: 4 mM

The reaction tube was irradiated under 365 nm UV, at 50° C., for 2 h. The reaction products were analyzed by SDS-PAGE.

Applications

Site-specifically modified proteins are invaluable reagents for studying the biology of protein lysine acetylation—an intensive field in biomedical research at present. However, as discussed above, these proteins are difficult to come by and none of them are available commercially. The presently disclosed method will make such proteins easily available, and an immediate application will be to produce these modified proteins as commercial products for the biomedical research community.

In the long term, since many proteins require modification on their structure to acquire desired activity and/or improved pharmacokinetic properties, the technology can be used to manufacture modified proteins with e.g., longer half-life for therapeutic applications.

Accordingly, in summary, the present disclosure provides a thiol-ene radical addition reaction involving, for instance, the commercially available NVA, which is well suited for the S-acetamidoethylation of cysteine residues in synthetic peptides and recombinant proteins. The resultant N-acetyl-thialysine differs with natural acetyl-lysine only isosterically at the γ-position of the amino acid structure and is functionally equivalent or similar to the latter.

The disclosed reaction and method has many potential applications, such as the histone epigenetic study. The disclosed reaction system is robust and gives near quantitative yields of site-specifically acetylated proteins which can be purified in a simple chromatography or dialysis step. The ease of implementation of this method also makes it easily adoptable by researchers from the bioscience research community. As such, this radical reaction approach provides a convenient enabling tool for the study of lysine acetylation biology and will help to advance research in this important field.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of alkylating a thiol group or a seleno group in a target molecule, the method comprising:
   a thiol-ene reaction comprising reacting said thiol or seleno group with a compound of formula (I) or (II):

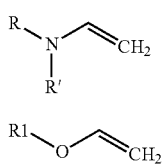

Wherein:
R is an acetyl group, an acyl group (other than acetyl), a poly(ethylene glycol)-containing acyl group ("PEG-containing acyl group") or is selected from the group consisting of:

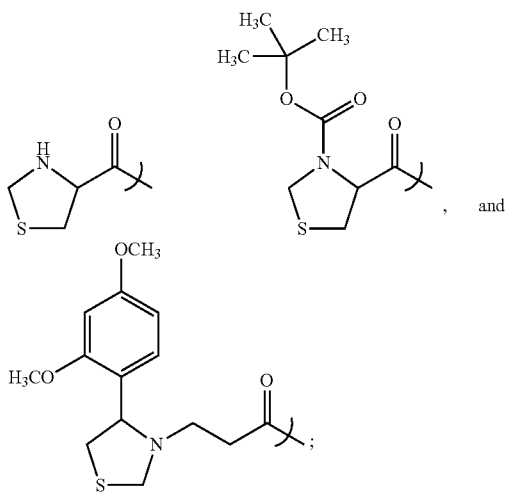

R1 is an alkyl group, an acyl group, PEG, or a PEG-containing acyl group;
and
R' is selected from the group consisting of a hydrogen, a methyl group and an ethyl group.

2. The method of claim 1, wherein said reacting step is performed in an acetate buffer.

3. The method of claim 2, wherein the target molecule is a peptide or protein.

4. The method of claim 3, wherein the peptide is selected from the group consisting of an oligopeptide, a polypeptide and a synthetic peptide.

5. The method of claim 3, wherein the protein is selected from the group consisting of a recombinant protein, a protein complex, a histone and a ubiquitin.

6. The method of claim 1, wherein the acyl group is an aliphatic acyl group, an alicyclic acyl group, an aromatic acyl group, an amino acyl group, a peptidyl group, or a proteinyl group.

7. The method of claim 1, wherein the acyl group is selected from the group consisting of a linear aliphatic acyl group, a branched aliphatic acyl group, a tert-butyloxycarbonyl group, a derivative of a tert-butyloxycarbonyl group, a benzyloxycarbonyl group and a derivative of a benzyloxycarbonyl group.

8. The method of claim 6, wherein the acyl group is selected from the group consisting of linear aliphatic acyl groups having 1 to 20 carbon atoms and branched aliphatic acyl groups having 1 to 7 carbon atoms.

9. The method of claim 6, wherein the acyl group is selected from the group consisting of a formyl group, a propionyl group, a 2-propionyl group, a butyryl group, an isobutyryl group, a pentanoyl group, a hexanoyl group, an allylcarbonyl group, a cyclohexylmethylcarbonyl group, and a $C_3$-$C_6$ cycloalkylcarbonyl group.

10. The method of claim 6, wherein the aromatic acyl group is selected from the group consisting of a benzoyl group, a 4-methylbenzoyl group, and a 4-methoxybenzoyl group.

11. The method of claim 1, wherein the alkyl group is selected from the group consisting of methyl, ethyl, n-propyl, i-propyl, n-butyl, t-butyl, sec-butyl, pentyl, hexyl, octyl, nonyl, decyl, undecyl, dodecyl, tridecyl, tetradecyl, pentadecyl, hexadecyl, and octadecyl, and wherein said poly(ethylene glycol) in said PEG-containing acyl group is poly(ethylene glycol)-ethyl or poly(ethylene glycol)-propyl.

12. A method of alkylating a target molecule comprising a thiol group or a seleno group, the method comprising: reacting the compound of Formula (I) as defined in claim 1 with the thiol or the seleno group of said target molecule to alkylate the target molecule via a thiol-ene reaction.

13. A method, comprising: reacting the compound of Formula (I) as defined in claim 1 with a target molecule having a thiol group or a seleno group to install an acetylated lysine residue analog in the target molecule via a thiol-ene reaction.

14. The method of claim 12, wherein the target molecule is an organic molecule selected from the group consisting of a peptide, an oligopeptide, a polypeptide, a synthetic peptide, a protein, a recombinant protein and a protein complex.

15. The method of claim 1 wherein the compound of formula (I) is N-vinylacetamide.

16. The method of claim 1, wherein the reaction step is performed in the presence of an additional thiol compound.

17. The method of claim 13, wherein the target molecule is an organic molecule selected from the group consisting of a peptide, an oligopeptide, a polypeptide, a synthetic peptide, a protein, a recombinant protein and a protein complex.

18. The method of claim 2, wherein the buffer is at a pH of 4.

* * * * *